(12) United States Patent
Hilpert et al.

(10) Patent No.: US 8,404,680 B2
(45) Date of Patent: Mar. 26, 2013

(54) N-[3-(5-AMINO-3,3A,7,7A-TETRAHYDRO-1H-2,4-DIOXA-6-AZA-INDEN-7-YL)-PHENYL]-AMIDES AS BACE1 AND/OR BACE2 INHIBITORS

(75) Inventors: Hans Hilpert, Muenchenstein (CH); Roland Humm, Auggen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/364,672

(22) Filed: Feb. 2, 2012

(65) Prior Publication Data

US 2012/0202803 A1 Aug. 9, 2012

(30) Foreign Application Priority Data

Feb. 8, 2011 (EP) .................................. 11153633

(51) Int. Cl.
*C07D 498/04* (2006.01)
*A61K 31/5365* (2006.01)
(52) U.S. Cl. ........................ 514/230.5; 544/91
(58) Field of Classification Search .................... 544/91; 514/230.5
See application file for complete search history.

(56) References Cited

U.S. PATENT DOCUMENTS

2011/0190279 A1    8/2011   Hori et al.

FOREIGN PATENT DOCUMENTS

| WO | 2009/151098 | 12/2009 |
| WO | 2011/071135 | 6/2011 |
| WO | WO 2011071135 A1 * | 6/2011 |

OTHER PUBLICATIONS

Selkoe et al., "Annual Review Cell Biology" 10:373-403 ( 1994).
Prentki et al., J. Clin. Investig. 116(7):1802-1812 ( 2006).
Luo et al., "Nat. Neuroscience" 4(3):231-232 ( 2001).
Zimmet et al., Nature 414:782-787 ( 2001).
McConlogue et al., "J. Biol. Chem." 282(36):26326-26334 ( 2007).
"International Search Report PCT/EP2012/051910—mailed Apr. 17, 2012".
Hardy et al., "Science" ((5580)), 297:353-356, (2002).
Baggio et al., Annu. Rev. Med. 57:265-281 ( 2006).
Wild et al., "Diabetes Care" 27(5):1047-1053 ( 2004).
Kuhn et al., "J. Biol. Chem." 282(16):11982-11995 ( 2007).
Hussain et al., "Mol. Cell Neurosci." 16:609-619 ( 2000).
Akpinar et al., Cell Metab. 2:385-397 ( 2005).
Finzi et al., "Ultrastruct. Pathol." 32(6):246-251 ( 2008).
Vassar et al., "Science" ((5440)), 286:735-741 ( 1999).
Fukui et al., "Cell Metabolism" 2:373-384 ( 2005).
Roberds et al., Hum. Mol. Genet. 10(12):1317-1324 ( 2001).

* cited by examiner

*Primary Examiner* — Kahsay T Habte
(74) *Attorney, Agent, or Firm* — George W. Johnston; Patricia S. Rocha-Tramaloni; Kimberly J. Prior

(57) ABSTRACT

The present invention relates to N-[3-(5-Amino-3,3a,7,7a-tetrahydro-1H-2,4-dioxa-6-aza-inden-7-yl)-phenyl]-amides of formula I

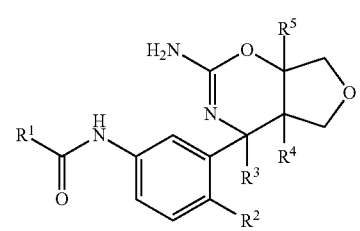

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

59 Claims, No Drawings

N-[3-(5-AMINO-3,3A,7,7A-TETRAHYDRO-1H-2,4-DIOXA-6-AZA-INDEN-7-YL)-PHENYL]-AMIDES AS BACE1 AND/OR BACE2 INHIBITORS

PRIORITY TO RELATED APPLICATION(S)

This application claims the benefit of European Patent Application No. 11153633.0, filed Feb. 8, 2011, which is hereby incorporated by reference in its entirety.

BACKGROUND ART

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science.* 2002 Jul. 19; 297(5580):353-6, Selkoe, Cell biology of the amyloid beta-protein precursor and the mechanism of Alzheimer's disease, *Annu Rev Cell Biol.* 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space; their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a pre-senilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science.* 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat. Neurosci.* 2001 March; 4(3):231-2, Roberds et al., BACE knockout mice are healthy despite lacking the primary beta-secretase activity in brain: implications for Alzheimer's disease therapeutics, *Hum Mol. Genet.* 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol. Chem.* 2007 Sep. 7; 282(36):26326). It is thus presumed that inhibitors of BACE1 activity can be useful agents for therapeutic intervention in Alzheimer's disease (AD).

Type 2 diabetes (T2D) is caused by insulin resistance and inadequate insulin secretion from pancreatic β-cells leading to poor blood-glucose control and hyperglycemia (M Prentki & CJ Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, KGMM Alberti & J Shaw, "Global and societal implications of the diabetes epidemic" Nature 2001, 414, 782-787).

β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu. Rev. Med. 2006, 57, 265-281).

Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients.

FIELD OF THE INVENTION

The present invention relates to N-[3-(5-Amino-3,3a,7,7a-tetrahydro-1H-2,4-dioxa-6-aza-inden-7-yl)-phenyl]-amides having BACE1 and/or BACE2 inhibitory properties, their manufacture, pharmaceutical compositions containing them and their use as therapeutically active substances.

SUMMARY OF THE INVENTION

The present invention relates to a compounds of formula I,

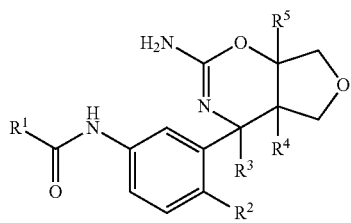

I wherein the substituents and variables are as described below and in the claims, or a pharmaceutically acceptable salt thereof.

The present compounds have Asp2 (β-secretase, BACE1 or Memapsin-2) inhibitory activity and BACE2 inhibitory activity. Compounds having Asp2 inhibitory activity can be used in the therapeutic and/or prophylactic treatment of diseases and disorders characterized by elevated β-amyloid levels and/or β-amyloid oligomers and/or β-amyloid plaques and further deposits, particularly Alzheimer's disease. Compounds having BACE2 inhibitory activity can be used in the therapeutic and/or prophylactic treatment of diseases and disorders such as type 2 diabetes and other metabolic disorders.

The invention provides selective BACE2 inhibitors. Such compounds are useful as therapeutically active substances, particularly in the treatment and/or prevention of diseases which are associated with the inhibition of BACE2. Furthermore, the formation, or formation and deposition, of β-amyloid peptides in, on or around neurological tissue (e.g., the brain) are inhibited by the present compounds, i.e. inhibition of the Aβ-production from APP or an APP fragment.

The present invention provides novel compounds of formula I, their manufacture, pharmaceutical compositions containing them, the production of such compounds and use of compounds of formula I in the control or prevention of illnesses such as Alzheimer's disease and type 2 diabetes.

DETAILED DESCRIPTION OF THE INVENTION

The present invention provides a compound of formula I and pharmaceutically acceptable salts thereof, the preparation of the above mentioned compounds, pharmaceutical compositions containing them and their manufacture as well as the use of the above mentioned compounds in the therapeutic and/or prophylactic treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

The term "$C_{1-6}$-alkyl", alone or in combination with other groups, stands for a hydrocarbon radical which is linear or branched, with single or multiple branching, wherein the alkyl group in general contains 1 to 6 carbon atoms, for example, methyl (Me), ethyl (Et), propyl, isopropyl (i-propyl), n-butyl, i-butyl (isobutyl), 2-butyl (sec-butyl), t-butyl (tert-butyl), isopentyl, 2-ethyl-propyl, 1,2-dimethyl-propyl and the like. Particular "$C_{1-6}$-alkyl" groups are those with 1 to 5 carbon atoms. Specific "$C_{1-6}$-alkyl" groups are methyl, ethyl and t-butyl—most specifically methyl.

The term "cyano-$C_{1-6}$-alkyl", alone or in combination with other groups, refers to $C_{1-6}$-alkyl as defined herein, which is substituted by one or multiple cyano groups, in particular 1-5 cyano, more particular 1 cyano. Examples are cyano-methyl and the like.

The term "halogen-$C_{1-6}$-alkyl", alone or in combination with other groups, refers to $C_{1-6}$-alkyl as defined herein, which is substituted by one or multiple halogen atoms, preferably 1-5 halogen atoms, more preferably 1-3 halogen atoms, most preferably 1 halogen atom or 3 halogen atoms. A particular halogen is fluoro. Examples of "halogen-$C_{1-6}$-alkyl" are difluoromethyl, chloromethyl, fluoromethyl and the like, in particular —$CH_2CH_2F$, $CH_2CHF_2$ or —$CF_3$. A specific example is trifluoromethyl.

The term "$C_{1-6}$-alkoxy-$C_{1-6}$-alkyl", alone or in combination with other groups, refers to $C_{1-6}$-alkyl, which is substituted by one or multiple $C_{1-6}$-alkoxy as defined herein. Examples are MeO-Me, 1MeO-Et, 2MeO-Et, 1MeO-2EtO-propyl and the like.

The term "cyano", alone or in combination with other groups, refers to N≡C—(NC—).

The term "halogen", alone or in combination with other groups, denotes chloro (Cl), iodo (I), fluoro (F) and bromo (Br). Particularly, "halogen" is Cl and F—specifically F.

The term "aryl", alone or in combination with other groups, refers to an aromatic carbocyclic group containing 6 to 14, preferably 6 to 10, ring carbon atoms and having at least one aromatic ring or multiple condensed rings in which at least one ring is aromatic. Examples of "aryl" include benzyl, biphenyl, indanyl, naphthyl, phenyl (Ph) and the like. Particularly, "aryl" is phenyl.

The term "heteroaryl", alone or in combination with other groups, refers to a cyclic aromatic group of having a single 4 to 8 membered ring or multiple condensed rings containing 6 to 14, in particular 6 to 10, ring atoms and containing 1, 2 or 3 heteroatoms individually selected from N, O and S, in particular N and O, in which group at least one heterocyclic ring is aromatic. Examples of "heteroaryl" include benzofuryl, benzoimidazolyl, 1H-benzoimidazolyl, benzooxazinyl, benzoxazolyl, benzothiazinyl, benzothiazolyl, benzothienyl, benzotriazolyl, furyl, imidazolyl, indazolyl, 1H-indazolyl, indolyl, isoquinolinyl, isothiazolyl, isoxazolyl, oxazolyl, pyrazinyl, pyrazolyl (pyrazyl), 1H-pyrazolyl, pyrazolo[1,5-a]pyridinyl, pyridazinyl, pyridinyl, pyrimidinyl, pyrrolyl, quinolinyl, tetrazolyl, thiazolyl, thienyl, triazolyl, 6,7-dihydro-5H-[1]pyrindinyl and the like. Particular "heteroaryl" are pyridinyl and pyrazinyl—specifically pyridin-2-yl and pyrazin-2-yl.

The term "$C_{1-6}$-alkoxy", alone or in combination with other groups, stands for an —O—$C_{1-6}$-alkyl radical wherein $C_{1-6}$-alkyl is as defined herein for example, methoxy (OMe, MeO), ethoxy (OEt, propoxy, isopropoxy (1-propoxy), n-butoxy, i-butoxy (iso-butoxy), 2-butoxy (sec-butoxy), t-butoxy (tert-butoxy), isopentyloxy (i-pentyloxy) and the like. Particular "$C_{1-6}$-alkoxy" groups are those with 1 to 4 carbon atoms—specifically methoxy, ethoxy and ethyoxy.

The term "halogen-$C_{1-6}$-alkoxy", alone or in combination with other groups, refers to $C_{1-6}$-alkoxy as defined herein, which is substituted by one or multiple halogens, in particular fluoro. Particular "halogen-$C_{1-6}$-alkoxy" are fluoro-$C_{1-6}$-alkoxy—specific 2,2,2-trifluoro-ethoxy-.

The term "$C_{2-6}$-alkynyl-$C_{1-6}$-alkoxy", alone or in combination with other groups, refers to $C_{1-6}$-alkoxy as defined herein, which is substituted by one or multiple $C_{2-6}$-alkynyl as defined herein. A particular "$C_{2-6}$-alkynyl-$C_{1-6}$-alkoxy" is 5-but-2-ynyloxy-pyrazine-2-yl.

The term "$C_{2-6}$-alkynyl", alone or in combination with other groups, denotes a monovalent linear or branched hydrocarbon group of 2 to 6 carbon atoms, in particular 2 to 4 carbon atoms, and containing one, two or three triple bonds. Examples of "$C_{2-6}$-alkynyl" include ethynyl, propynyl, prop-2-ynyl, isopropynyl and n-butynyl. Specific "$C_{2-6}$-alkynyl" are ethynyl and propynyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Preferred are formic acid, trifluoroacetic acid and hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "inhibitor" denotes a compound which competes with, reduces or prevents the binding of a particular ligand to particular receptor or which reduces or prevents the inhibition of the function of a particular protein.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values (−log $IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there can be one or more intermediates which are produced in the mixture which ultimately leads to the formation of the indicated and/or the desired product.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

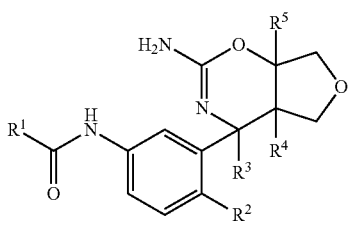

wherein
$R^1$ is selected from the group consisting of
i) aryl,
ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
iii) heteroaryl, and
iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
$R^2$ is selected from the group consisting of
i) hydrogen,
ii) $C_{1-6}$-alkyl, and
iii) halogen;
$R^3$ is selected from the group consisting of
i) $C_{1-6}$-alkyl, and
ii) halogen-$C_{1-6}$-alkyl;
$R^4$ is selected from the group consisting of
i) hydrogen, and
iv) $C_{1-6}$-alkyl; and
$R^5$ is selected from the group consisting of
i) hydrogen,
ii) halogen-$C_{1-6}$-alkyl, and
iii) $C_{1-6}$-alkyl;
or pharmaceutically acceptable salts thereof.

A certain embodiment of the invention is a compound of formula I,

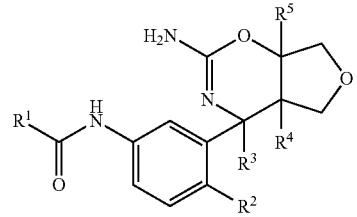

wherein
$R^1$ is selected from the group consisting of
i) aryl,
ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
iii) heteroaryl, and
iv) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
$R^2$ is selected from the group consisting of
i) hydrogen,
ii) $C_{1-6}$-alkyl, and
iii) halogen;
$R^3$ is $C_{1-6}$-alkyl;
$R^4$ is selected from the group consisting of
i) hydrogen, and
ii) $C_{1-6}$-alkyl; and
$R^5$ is selected from the group consisting of
i) hydrogen, and
ii) $C_{1-6}$-alkyl;
or pharmaceutically acceptable salts thereof.

A certain embodiment of the invention relates to compound of formula Ia,

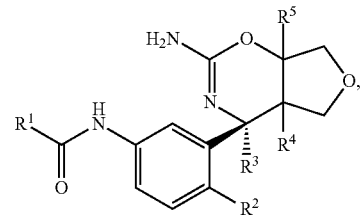

wherein $R^1$, $R^2$, $R^3$, $R^4$ and $R^5$ are as defined herein; or pharmaceutically acceptable salts thereof.

A certain embodiment of the invention is a compound of formula Ib,

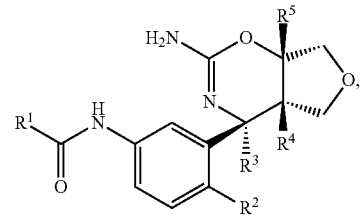

wherein $R^1$, $R^2$, $R^3$, $R^4$ and $R^5$ are as defined herein; or pharmaceutically acceptable salts thereof.

A certain embodiment of the invention provides a compound as defined herein, wherein $R^2$ is halogen.

A certain embodiment of the invention provides a compound as defined herein, wherein $R^2$ is F.

A certain embodiment of the invention provides a compound as defined herein, wherein $R^3$ is $C_{1-6}$-alkyl or halogen-$C_{1-6}$-alkyl.

A certain embodiment of the invention provides a compound as defined herein, wherein $R^3$ is $C_{1-6}$-alkyl.

A certain embodiment of the invention provides a compound as defined herein, wherein $R^3$ is methyl.

A certain embodiment of the invention provides a compound as defined herein, wherein $R^3$ is halogen-$C_{1-6}$-alkyl.

A certain embodiment of the invention provides a compound as defined herein, wherein $R^3$ is —$CH_2CH_2F$ or —$CH_2CHF_2$.

A certain embodiment of the invention provides a compound as defined herein, wherein $R^3$ is —$CH_2CH_2F$.

A certain embodiment of the invention provides a compound as defined herein, wherein $R^3$ is —$CH_2CHF_2$.

A certain embodiment of the invention provides a compound as defined herein, wherein $R^3$ is methyl, —$CH_2CH_2F$ or —$CH_2CHF_2$.

A certain embodiment of the invention provides a compound as defined herein, wherein $R^4$ is $C_{1-6}$-alkyl A certain embodiment of the invention provides a compound as defined herein, wherein $R^4$ is hydrogen.

A certain embodiment of the invention provides a compound as defined herein, wherein $R^5$ is hydrogen.

A certain embodiment of the invention provides a compound as defined herein, wherein $R^5$ is $C_{1-6}$-alkyl.

A certain embodiment of the invention provides a compound as defined herein, wherein $R^5$ is halogen-$C_{1-6}$-alkyl A certain embodiment of the invention provides a compound as defined herein, wherein $R^5$ is —$CF_3$.

A certain embodiment of the invention provides a compound as defined herein, wherein $R^1$ is heteroaryl or heteroaryl substituted by 1-2 substituents individually selected from cyano, halogen, halogen-$C_{1-6}$-alkoxy and $C_{2-6}$-alkynyl-$C_{1-6}$-alkoxy.

A certain embodiment of the invention provides a compound as defined herein, wherein $R^1$ is heteroaryl.

A certain embodiment of the invention provides a compound as defined herein, wherein $R^1$ is pyridinyl.

A certain embodiment of the invention provides a compound as defined herein, wherein R1 is pyridine-2-yl.

A certain embodiment of the invention provides a compound as defined herein, wherein $R^1$ is heteroaryl substituted by 1-2 substituents individually selected from cyano, halogen, halogen-$C_{1-6}$-alkoxy and $C_{2-6}$-alkynyl-$C_{1-6}$-alkoxy.

A certain embodiment of the invention provides a compound as defined herein, wherein $R^1$ is pyridinyl substituted by 1-2 substituents individually selected from cyano, halogen and halogen-$C_{1-6}$-alkoxy.

A certain embodiment of the invention provides a compound as defined herein, wherein $R^1$ is 5-chloro-pyridine-2-yl.

A certain embodiment of the invention provides a compound as defined herein, wherein $R^1$ is 3,5-dichloro-pyridine-2-yl.

A certain embodiment of the invention provides a compound as defined herein, wherein $R^1$ is 5-(2,2,2-trifluoro-ethoxy)-pyridine-2-yl.

A certain embodiment of the invention provides a compound as defined herein, wherein $R^1$ is 5-cyano-pyridine-2-yl.

A certain embodiment of the invention provides a compound as defined herein, wherein $R^1$ is 5-fluoro-pyridine-2-yl.

A certain embodiment of the invention provides a compound as defined herein, wherein $R^1$ is pyrazinyl substituted by halogen-$C_{1-6}$-alkoxy or $C_{2-6}$-alkynyl-$C_{1-6}$-alkoxy.

A certain embodiment of the invention provides a compound as defined herein, wherein $R^1$ is 5-(2,2,2-trifluoro-ethoxy)-pyrazine-2-yl.

A certain embodiment of the invention provides a compound as defined herein, wherein $R^1$ is 5-but-2-ynyloxy-pyrazine-2-yl.

A certain embodiment of the invention provides a compound as defined herein, wherein $R^1$ is pyridinyl, pyridinyl substituted by 1-2 substituents individually selected from cyano, halogen and halogen-$C_{1-6}$-alkoxy or pyrazinyl substituted by halogen-$C_{1-6}$-alkoxy or $C_{2-6}$-alkynyl-$C_{1-6}$-alkoxy.

A certain embodiment of the invention provides a compound as defined herein, wherein $R^1$ is 5-chloro-pyridine-2-yl, 3,5-dichloro-pyridine-2-yl, 5-(2,2,2-trifluoro-ethoxy)-pyrazine-2-yl, 5-(2,2,2-trifluoro-ethoxy)-pyridine-2-yl, 5-but-2-ynyloxy-pyrazine-2-yl, 5-cyano-pyridine-2-yl, 5-fluoro-pyridine-2-yl or pyridine-2-yl.

A certain embodiment of the invention provides a compound as defined herein, wherein $R^1$ is $R^1$ is 5-cyano-pyridine-2-yl or 5-but-2-ynyloxy-pyrazine-2-yl.

A certain embodiment of the invention provides a compound as defined herein, wherein $R^1$ is aryl.

A certain embodiment of the invention provides a compound as defined herein, wherein $R^1$ is aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl.

A certain embodiment of the invention provides a compound as described herein, selected from the group consisting of 5-Chloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-Fluoro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-Cyano-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-But-2-ynyloxy-pyrazine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-Cyclopropylmethoxy-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-But-2-ynyloxy-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-Cyano-pyridine-2-carboxylic acid [3-((3aS,7S,7aS)-5-amino-7-fluoromethyl-3,3a,7,7a-tetrahydro-1H-2,4-dioxa-6-aza-inden-7-yl)-4-fluoro-phenyl]-amide, 5-Chloro-pyridine-2-carboxylic acid [3-((3aS,7S,7aS)-5-amino-7-fluoromethyl-3,3a,7,7a-tetrahydro-1H-2,4-dioxa-6-aza-inden-7-yl)-4-fluoro-phenyl]-amide, 5-Fluoro-pyridine-2-carboxylic acid [3-((3aS,7S,7aS)-5-amino-7-fluoromethyl-3,3a,7,7a-tetrahydro-1H-2,4-dioxa-6-aza-inden-7-yl)-4-fluoro-phenyl]-amide, 5-Chloro-pyridine-2-carboxylic acid [3-((3aS,7S,7aS)-5-amino-7-difluoromethyl-3,3a,7,7a-tetrahydro-1H-2,4-dioxa-6-aza-inden-7-yl)-4-fluoro-phenyl]-amide,
5-Cyano-pyridine-2-carboxylic acid [3-((3aS,7S,7aS)-5-amino-7-difluoromethyl-3,3a,7,7a-tetrahydro-1H-2,4-dioxa-6-aza-inden-7-yl)-4-fluoro-phenyl]-amide,
5-But-2-ynyloxy-pyrazine-2-carboxylic acid [3-((3aS,7S,7aS)-5-amino-7-difluoromethyl-3,3a,7,7a-tetrahydro-1H-2,4-dioxa-6-aza-inden-7-yl)-4-fluoro-phenyl]-amide,
N-(3-(rel-(4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-cyanopicolinamide,
N-(3-(rel-(4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-(but-2-ynyloxy)pyrazine-2-carboxamide,
N-(3-((4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-chloropicolinamide,
N-(3-((4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-cyanopicolinamide,
5-(2,2,2-Trifluoro-ethoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
5-(2,2,2-Trifluoro-ethoxy)-pyrazine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
5-(2,2,3,3-Tetrafluoro-propoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
N-(3-((4S,4aS,7aS)-2-amino-4-methyl-4a,5,7,7a-tetrahydro-4H-furo[3,4-e][1,3]oxazin-4-yl)-4-fluorophenyl)-3-chloro-5-cyanopicolinamide,
Pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, and
3,5-Dichloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
or a pharmaceutical acceptable salt thereof.

A certain embodiment of the invention provides a compound as described herein, selected from the group consisting of
5-Chloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
3,5-Dichloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
5-(2,2,2-Trifluoro-ethoxy)-pyrazine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
5-(2,2,2-Trifluoro-ethoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
5-But-2-ynyloxy-pyrazine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
5-Cyano-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
5-Fluoro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, and
Pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide,
or a pharmaceutical acceptable salt thereof.

A certain embodiment of the invention provides a process to synthesize a compound of formula I as described herein, which process comprises reacting a compound of formula XI with a compound of formula XII to a compound of formula I

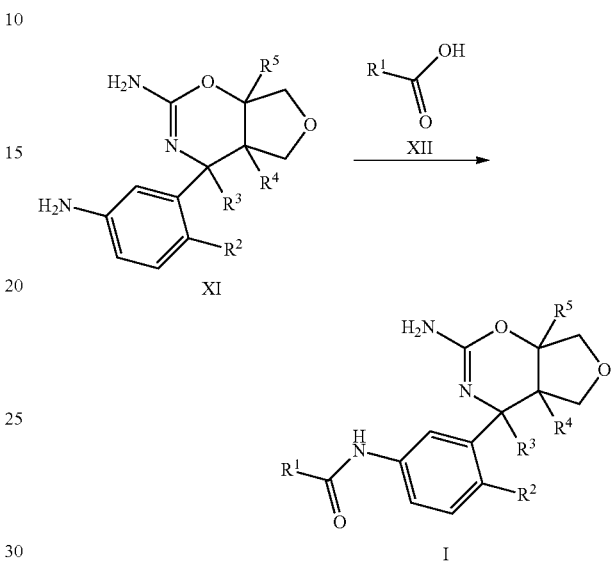

wherein R', $R^2$, $R^3$, $R^4$, $R^5$ are as defined herein.

A certain embodiment of the invention relates to a compound of formula I as described herein, whenever prepared by a process as defined above.

A certain embodiment of the invention relates to a compound of formula I as described herein for use as therapeutically active substance.

A certain embodiment of the invention relates to a compound of formula I as described herein for the use as inhibitor of BACE1 and/or BACE2 activity.

A certain embodiment of the invention relates to a compound of formula I as described herein for the use as inhibitor of BACE1 activity.

A certain embodiment of the invention relates to a compound of formula I as described herein for the use as inhibitor of BACE2 activity.

A certain embodiment of the invention relates to a compound of formula I as described herein for the use as inhibitor of BACE1 and BACE2 activity.

A certain embodiment of the invention relates to a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention relates to a compound of formula I as described herein for the use as therapeutically active substance for the therapeutic and/or prophylactic treatment of Alzheimer's disease.

A certain embodiment of the invention relates to a compound of formula I as described herein for the use as therapeutically active substance for the therapeutic and/or prophylactic treatment of diabetes, particularly type 2 diabetes.

A certain embodiment of the invention relates to a compound of formula I as described herein for the use as therapeutically active substance for the therapeutic and/or prophylactic treatment of diabetes.

A certain embodiment of the invention relates to a pharmaceutical composition comprising a compound of formula I as described herein and a pharmaceutically acceptable carrier and/or a pharmaceutically acceptable auxiliary substance.

A certain embodiment of the invention relates to the use of a compound of formula I as described herein for the manufacture of a medicament for the use in inhibition of BACE1 and/or BACE2 activity.

A certain embodiment of the invention relates to the use of a compound of formula I as described herein for the manufacture of a medicament for the use in inhibition of BACE1 activity.

A certain embodiment of the invention relates to the use of a compound of formula I as described herein for the manufacture of a medicament for the use in inhibition of BACE2 activity.

A certain embodiment of the invention relates to the use of a compound of formula I as described herein for the manufacture of a medicament for the use in inhibition of BACE1 and BACE2 activity.

A certain embodiment of the invention relates to the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention relates to the use of a compound of formula I as described herein for the manufacture of a medicament for the therapeutic and/or prophylactic treatment of Alzheimer's disease.

A certain embodiment of the invention relates to the use of a compound of formula I as described herein for the manufacture of a medicament for the therapeutic and/or prophylactic treatment of diabetes, particularly type 2 diabetes.

A certain embodiment of the invention relates to the use of a compound of formula I as described herein for the manufacture of a medicament for the therapeutic and/or prophylactic treatment of diabetes.

A certain embodiment of the invention relates to a compound of formula I as described herein for the use in inhibition of BACE1 and/or BACE2 activity.

A certain embodiment of the invention relates to a compound of formula I as described herein for the use in inhibition of BACE1 activity.

A certain embodiment of the invention relates to a compound of formula I as described herein for the use in inhibition of BACE2 activity.

A certain embodiment of the invention relates to a compound of formula I as described herein for the use in inhibition of BACE1 and BACE2 activity.

A certain embodiment of the invention relates to a compound of formula I as described herein for the use in the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention relates to a compound of formula I as described herein for the use in the therapeutic and/or prophylactic treatment of Alzheimer's disease.

A certain embodiment of the invention relates to a compound of formula I as described herein for the use in the therapeutic and/or prophylactic treatment of diabetes, particularly type 2 diabetes.

A certain embodiment of the invention relates to a compound of formula I as described herein for the use in the therapeutic and/or prophylactic treatment of diabetes.

A certain embodiment of the invention relates to a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

A certain embodiment of the invention relates to a method for the use in the therapeutic and/or prophylactic treatment of Alzheimer's disease, diabetes or type 2 diabetes, which method comprises administering compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates of the compounds of formula I.

The skilled person in the art will recognize that the compounds of formula I can exist in tautomeric forms, e.g. in the following tautomeric form.

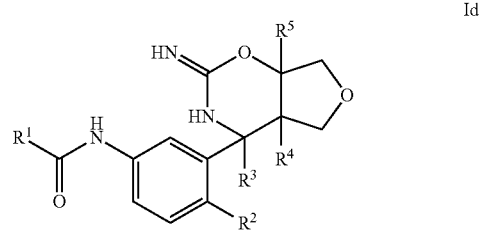

Id

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric center will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric center of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Preferred examples of isomers of a compound of formula I is a compound of formula Ib or a compound of formula Ic, in particular Ib, wherein the residues have the meaning as described in any of the embodiments.

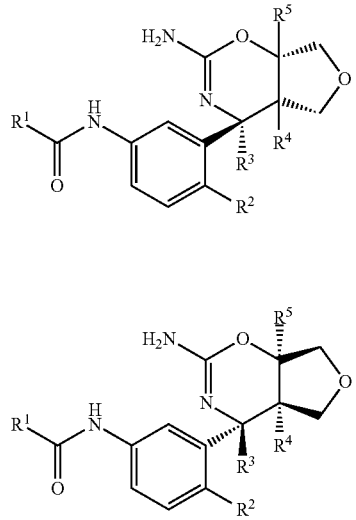

In the embodiments, where optically pure enantiomers are provided, optically pure enantiomer means that the compound contains >90% of the desired isomer by weight, preferably >95% of the desired isomer by weight, or more preferably >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following scheme. The starting material is commercially available or can be prepared in accordance with known methods. Any previously defined residues and variables will continue to have the previously defined meaning unless otherwise indicated.

The nitro compound (II) is reacted with olefine (III) in the presence of an activating reagent such as e.g. an isocyanate, in particular phenylisocyanate and a catalytic amount of a base, in particular an alkyl amine, more particular NEt₃, in a solvent such as benzene or toluene, in particular benzene, or an alkyl ether, in particular diethyl ether to give the dihydroisoxazole IV.

Arylation of the dihydroisoxazole (IV) with the arylbromide (V) to give the isoxazolidine (VI) is performed by reacting an arylhalogenide, in particular an arylbromide with an alkyl lithium reagent, in particular n-BuLi to give an aryllithium species, which can be reacted with the dihydroisoxazole (IV) in the presence of a Lewis base, preferably boron trifluoride etherate in a solvent mixture consisting of an ether, in particular THF and toluene at −100° C. to −20° C., in particular at −78° C.

Resolution of the racemic isoxazolidine (VI) to give the chiral isoxazolidine (VII) can be done by chiral high-performance liquid chromatography (HPLC) using a Chiralpack AD column in a mixture of n-heptane and ethanol.

Hydrogenolysis of the chiral isoxazolidine (VII) to the aminoalcohol (VIII) can be accomplished best by transfer hydrogenolysis using a Pd-catalyst, in particular Pd on carbon and a hydrogen source, e.g. a salt of formic acid, in particular ammonium formate in a protic solvent such as an alcohol, in particular ethanol.

Oxazine (IX) can be prepared by reaction of aminoalcohol (VIII) with cyanogen bromide in a solvent such as an alcohol, in particular ethanol at elevated temperature. Alternatively, the reaction can be carried out in two step sequence using cyanobromide and a buffer such as e.g. sodium acetate in the presence of a solvent such as e.g. CH₃CN followed by cyclization of the intermediate in the presence of a mineral acid, in particular hydrochloric acid in a solvent such as an ether, in particular 1,4dioxane.

The nitration of the oxazine (IX) to give the nitro-oxazine (X) follows a standard procedure involving neat sulfuric acid and fuming nitric acid without using a solvent.

The reduction of the nitro group in the intermediate (X) to give the aniline (XI) can be accomplished by hydrogenation using a catalyst such as Pd/C in protic solvents, such as alcohols, in particular ethanol and methanol.

Selective amide coupling of the aniline (XI) and a carboxylic acid (XII) to give the amide (I) can be effected with 4-(4,6-dimethoxy[1.3.5]triazin-2-yl)-4-methylmorpholinium chloride (DMTMM) hydrate in a solvent such as an alcohol, in particular methanol.

Scheme 1: Synthesis of compounds of formula I with R² = F, R³ = methyl, R⁴ = H and R⁵ = H (I').

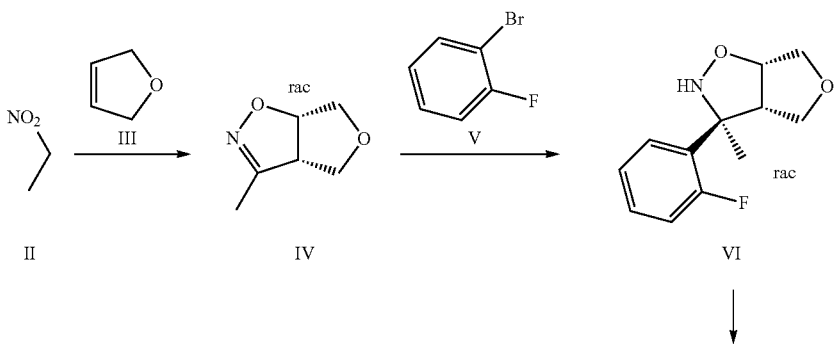

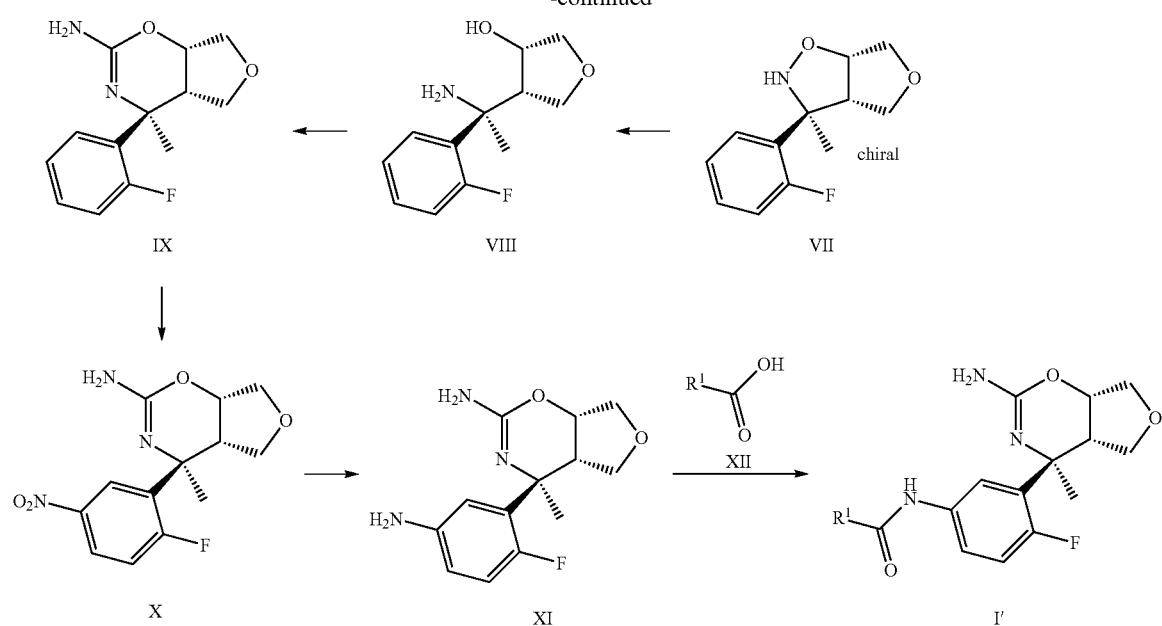
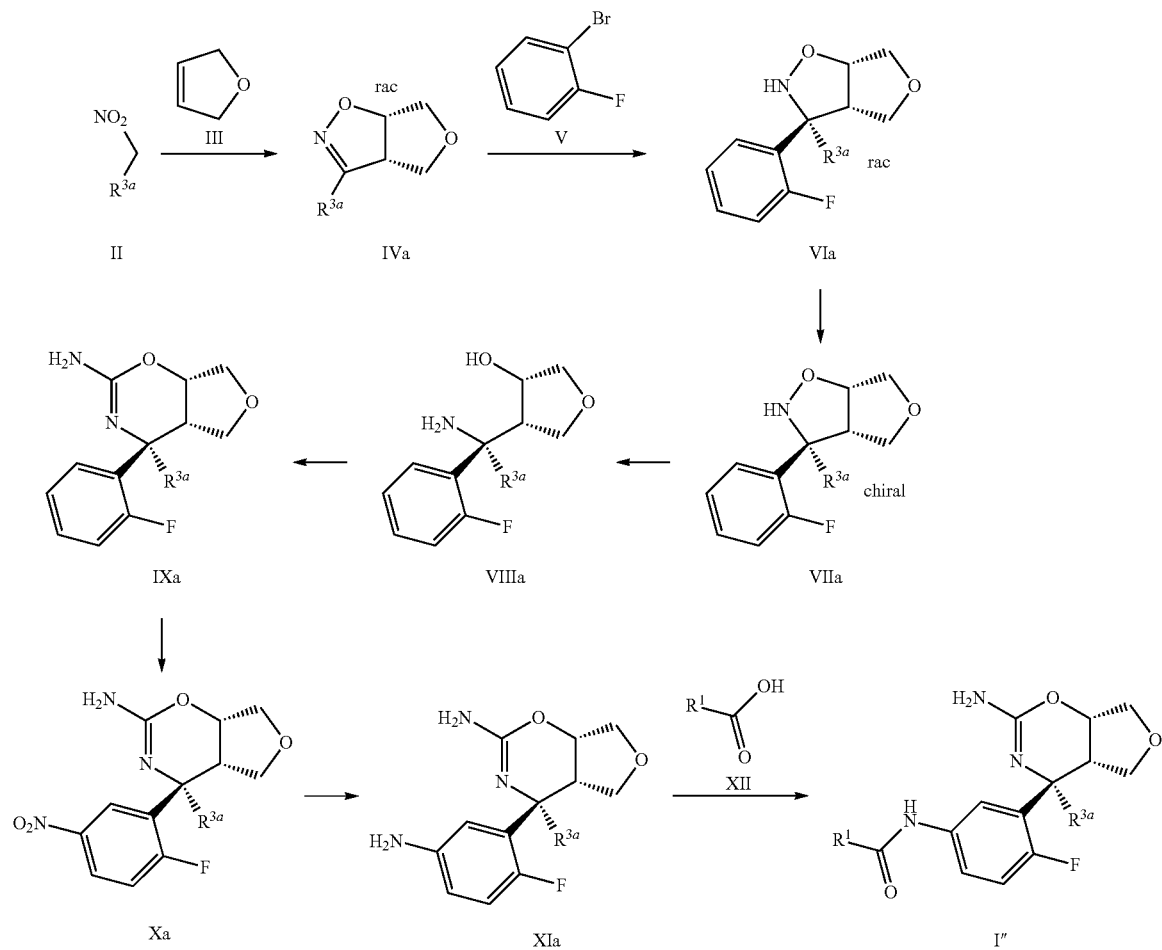
Scheme 2: Synthesis of compounds of formula I with $R^2$ = F, $R^3$ = methyl, (I″).

Scheme 3: Synthesis of compounds of formula I''' with R² = F.
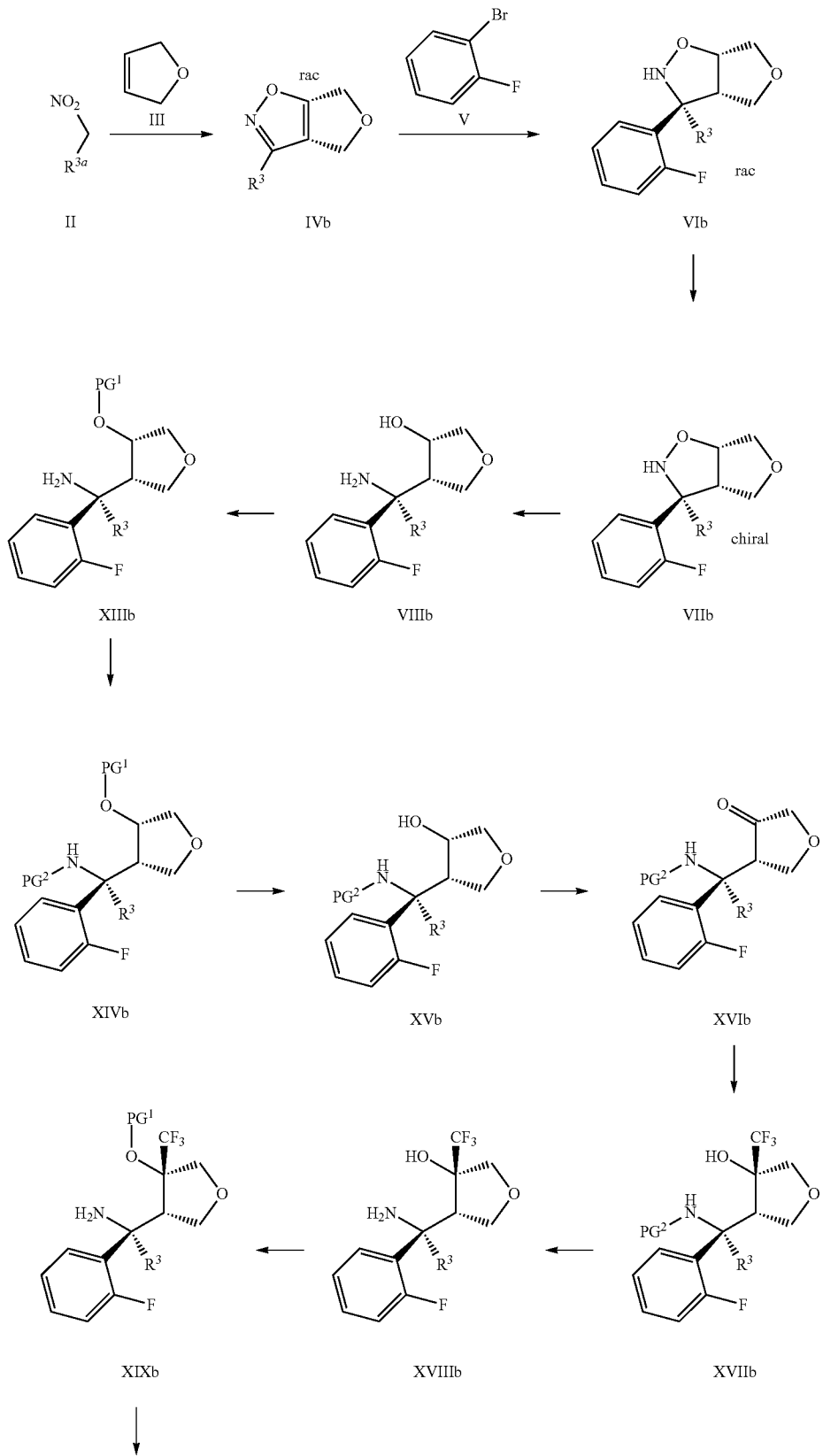

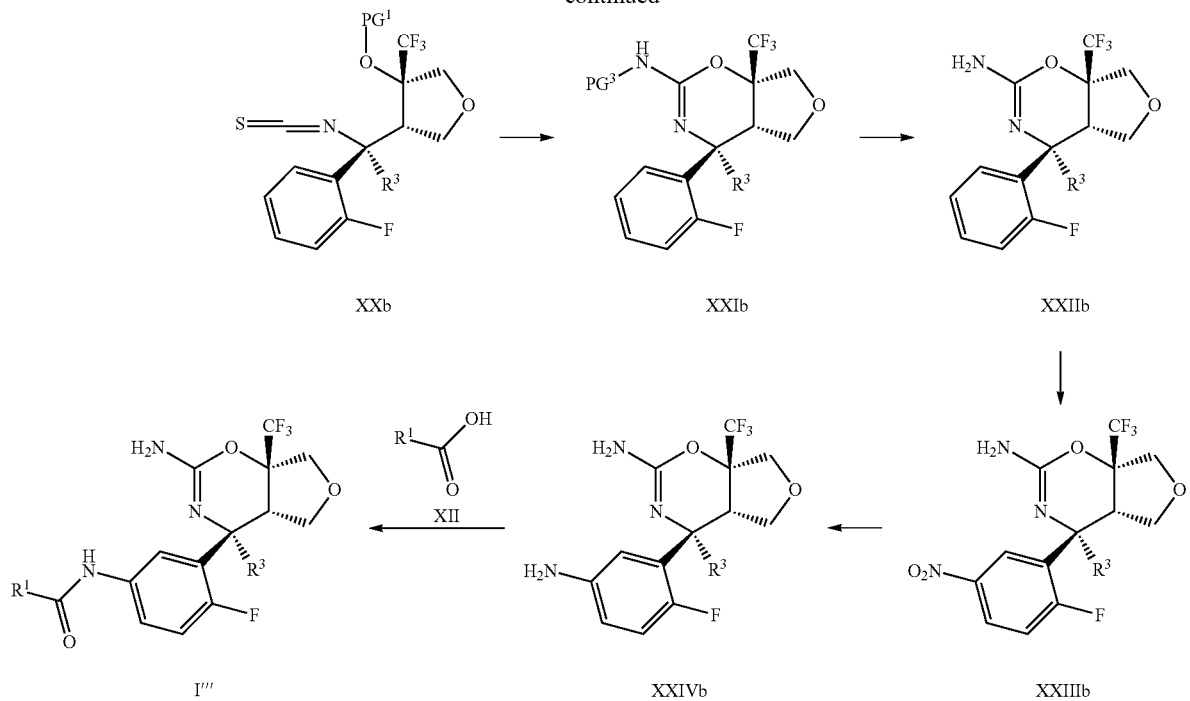

Compounds of formula I''' can be prepared as depicted in scheme 3. The already above described aminoalcohol VIIIb can be selectively protected on the oxygen by O-silylation to the O-silylated aminoalcohol XIIIb with a chlorosilane, in particular tert-butylchlorodimethylsilane (PG$^1$=t-BuMe$_2$Si), in a chlorinated solvent such as dichloromethane in the presence of an trialkylamine base, in particular triethylamine, and a pyridine catalyst, in particular 4-dimethylaminopyridine, at 0° C. to 23° C.

The O-silylated aminoalcohol XIIIb can be acylated to the O-silylated N-sulfinylated aminoalcohol XIVb with an sulfinyl chloride, in particular tert-butylsulfinyl chloride (PG$^2$=t-BuSO, in a chlorinated solvent, in particular dichloromethane, in the presence of a an amine base, such as triethylamine or diisopropylethylamine, at 0° C. to 60° C., preferably 23° C.

The O-silylated N-sulfinylated aminoalcohol XIVb can be desilylated to the N-sulfinylated aminoalcohol XVb by reacting it with a fluoride source, in particular tetrabutylammonium fluoride (TBAF), in a solvent such as THF at 0° C. to 50° C., preferably at 23° C.

The N-sulfinylated aminoalcohol XVb can be oxidized to the N-sulfinylated aminoketone XVIb by a combination of reagents such as oxalyl chloride, dimethylsulfoxide and an amine base, such as triethylamine or diisopropylamine, in a chlorinated solvent, in particular dichloromethane, at temperatures from –78° C. to ambient temperature.

The N-sulfinylated aminoketone XVIb can be transformed to the N-sulfinylated amino-α-trifluoromethylalcohol XVIIb by reacting it with a trifluoromethylating reagent, such as (trifluoromethyl)trimethylsilane (Ruppert's reagent), in the presence of a fluoride source, in particular tetrabutylammonium fluoride (TBAF), in a solvent such as THF at 0° C. to 50° C., preferably at 0 to 23° C.

The N-sulfinylated amino-α-trifluoromethylalcohol XVIIb can be deprotected to the amino-α-trifluoromethylalcohol XVIIIb by reaction with a strong aqueous mineral acid, in particular hydrochloric acid, in solvents such as THF, ethyl acetate, methanol or ethanol, at temperatures between 0 and 23° C.

The amino-α-trifluoromethylalcohol XVIIIb can be selectively protected on the oxygen by O-silylation to the O-silylated amino-α-trifluoromethylalcohol XIXb with a strong silylating reagent, in particular tert-butyldimethylsilyltrifluoromethanesulfonate (PG$^1$=t-BuMe$_2$Si), in an etheral solvent such as THF in the presence of a strong base, in particular sodium hydride, at temperatures between 0° C. to 23° C.

The O-silylated amino-α-trifluoromethylalcohol XIXb can be transformed into the O-silylated α-trifluoromethylalcohol isothiocyanate XXb by treatment with thiophosgene or an equivalent reagent, such as 1,1'-thiocarbonyldiimidazole, in the presence of a weak base, such as sodium bicarbonate, in a chlorinated solvent, in particular dichloromethane, at temperatures between 0 and 23° C., preferably 23° C.

The O-silylated α-trifluoromethylalcohol isothiocyanate XXb can be converted into the N-benzylated oxazine XXIb by a three-step one-pot procedure as follows: 1.) reaction with an amine, in particular p-methoxybenzylamine (PG$^3$=PMB) or 2,4-dimethoxybenzylamine (PG$^3$=DMB), to the corresponding O-silylated thiourea in a solvent, in particular acetonitrile, at 0° C. to 100° C., preferably 80° C. 2.) The O-silylated thiourea can be desilylated to the α-trifluoromethylalcohol thiourea by reacting it with a fluoride source, in particular tetrabutylammonium fluoride trihydrate (TBAF.3H$_2$O), in a solvent such as acetonitrile at 0° C. to 80° C., preferably at 23° C. 3.) The α-trifluoromethylalcohol thiourea can be cyclized to the N-benzylated oxazine XXIb by treatment with a carbodiimide, such as dicyclohexylcarbodiimide, diisopropylcarbodiimide or 1-(3-dimethylaminopropyl)-3-ethylcarbodiimide hydrochloride, in a solvent such as acetonitrile at 23 to 100° C., preferably 80° C.

The N-benzylated oxazine XXIb is debenzylated to the oxazine XXIIb by neat reaction with a strong organic acid, in particular trifluoroacetic acid, at temperatures between 0° C. and 50° C., preferably at 23° C.

The oxazine XXIIb can be converted via the nitro-oxazine XXIIIb and the aniline XXIVb to the compounds of formula I''' as already described above for the oxazines IX and IXa.

Insofar as their preparation is not described in the examples, the compounds of formula I as well as all intermediate products can be prepared according to analogous methods or according to the methods set forth herein. Starting materials are commercially available, known in the art or can be prepared by methods known in the art or in analogy thereto.

It will be appreciated that the compounds of formula I in this invention can be derivatized at functional groups to provide derivatives which are capable of conversion back to the parent compound in vivo.

Pharmacological Tests

The compounds of formula I and their pharmaceutically acceptable salts possess valuable pharmacological properties. The compounds of the present invention are associated with inhibition of BACE1 and/or BACE2 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in $\frac{1}{10}$ volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Md. Heights, Mo.) and incubated for 5 to 7 hrs. Subsequently the wells of the microtiter plate were washed extensively with Tris-buffered saline containing 0.05% Tween 20 and the assay was developed with tetramethylbenzidine/$H_2O_2$ in citric acid buffer. After stopping the reaction with one volume 1 $NH_2SO_4$ the reaction was measured in an ELISA reader at 450 nm wavelength. The concentrations of Aβ in the culture supernatants were calculated from a standard curve obtained with known amounts of pure Aβ peptide.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+ Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator.

INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

TABLE 1

| | IC$_{50}$ values of selected examples | | |
|---|---|---|---|
| Exam. | Structure | BACE1 IC$_{50}$ [μM] | BACE2 IC$_{50}$ [μM] |
| 1 | 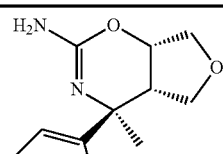 | 0.0007 | 0.036 |
| 2 | 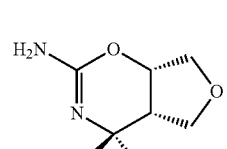 | 0.0008 | 0.014 |

TABLE 1-continued

IC₅₀ values of selected examples

| Exam. | Structure | BACE1 IC$_{50}$ [μM] | BACE2 IC$_{50}$ [μM] |
|---|---|---|---|
| 3 | 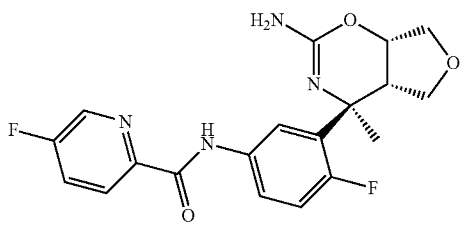 [SMILES: C[C@]1(c2cc(NC(=O)c3ccc(F)cn3)ccc2F)N=C(N)O[C@@H]2COC[C@@H]21] | 0.0025 | 0.018 |
| 4 | 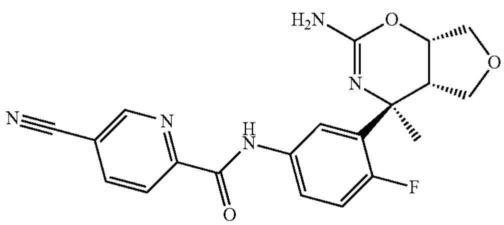 [SMILES: C[C@]1(c2cc(NC(=O)c3ccc(C#N)cn3)ccc2F)N=C(N)O[C@@H]2COC[C@@H]21] | — | 0.017 |
| 5 | 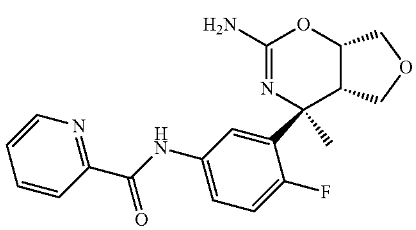 [SMILES: C[C@]1(c2cc(NC(=O)c3ccccn3)ccc2F)N=C(N)O[C@@H]2COC[C@@H]21] | 0.008 | 0.037 |
| 6 | 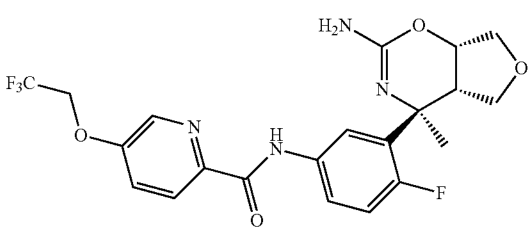 [SMILES: C[C@]1(c2cc(NC(=O)c3ccc(OCC(F)(F)F)cn3)ccc2F)N=C(N)O[C@@H]2COC[C@@H]21] | 0.006 | 0.556 |
| 7 | 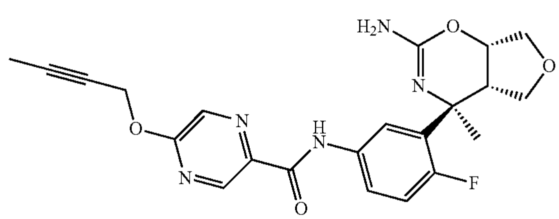 [SMILES: CC#CCOc1cnc(C(=O)Nc2ccc(F)c([C@@]3(C)N=C(N)O[C@@H]4COC[C@@H]43)c2)cn1] | — | 0.047 |
| 8 | 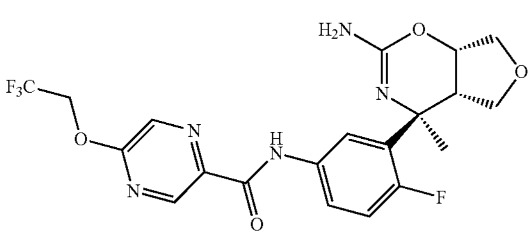 | 0.0018 | 0.209 |

TABLE 1-continued

IC$_{50}$ values of selected examples

| Exam. | Structure | BACE1 IC$_{50}$ [μM] | BACE2 IC$_{50}$ [μM] |
|---|---|---|---|
| 9 | 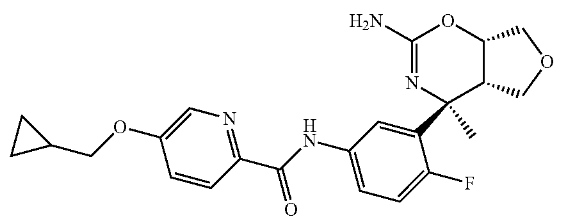 [SMILES: C[C@]1(c2cc(NC(=O)c3ccc(OCC4CC4)cn3)ccc2F)N=C(N)O[C@@H]2COC[C@@H]21] | 0.005 | — |
| 10 | 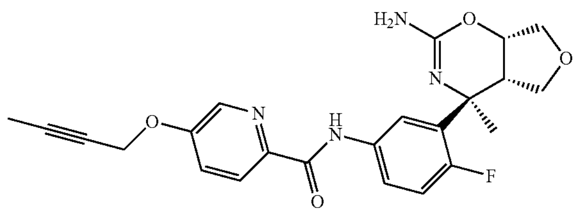 [SMILES: CC#CCOc1ccc(C(=O)Nc2ccc(F)c([C@@]3(C)N=C(N)O[C@@H]4COC[C@@H]43)c2)nc1] | 0.0001 | — |
| 11 | 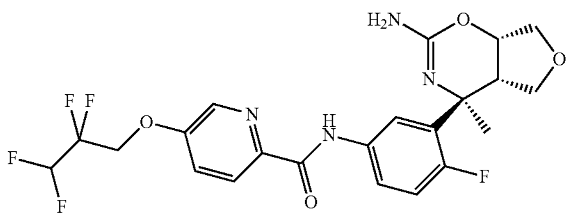 [SMILES: C[C@]1(c2cc(NC(=O)c3ccc(OCC(F)(F)C(F)F)cn3)ccc2F)N=C(N)O[C@@H]2COC[C@@H]21] | 0.005 | — |
| 12 | 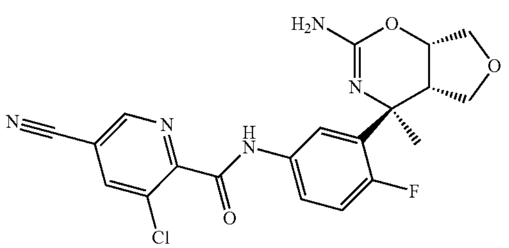 [SMILES: C[C@]1(c2cc(NC(=O)c3ncc(C#N)cc3Cl)ccc2F)N=C(N)O[C@@H]2COC[C@@H]21] | 0.001 | — |
| 13 | 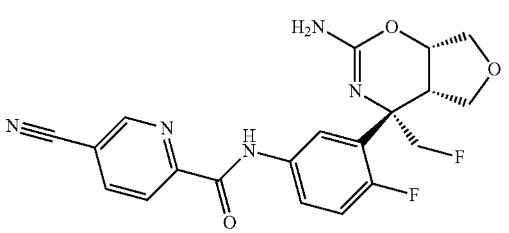 [SMILES: N#Cc1ccc(C(=O)Nc2ccc(F)c([C@@]3(CF)N=C(N)O[C@@H]4COC[C@@H]43)c2)nc1] | 0.001 | — |
| 14 | 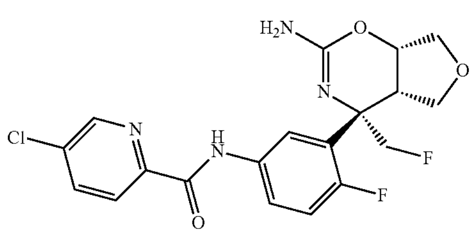 [SMILES: NC1=N[C@](CF)(c2cc(NC(=O)c3ccc(Cl)cn3)ccc2F)[C@H]2COC[C@H]2O1] | 0.001 | — |

TABLE 1-continued

IC$_{50}$ values of selected examples

| Exam. | Structure | BACE1 IC$_{50}$ [μM] | BACE2 IC$_{50}$ [μM] |
|---|---|---|---|
| 15 | 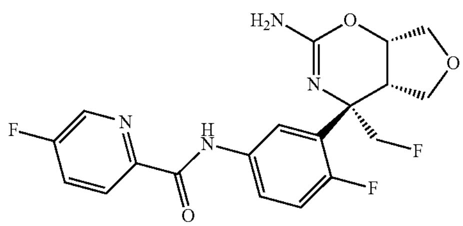 [SMILES: NC1=N[C@](CF)(c2cc(NC(=O)c3ccc(F)cn3)ccc2F)[C@H]2COC[C@H]2O1] | 0.0025 | — |
| 16 | 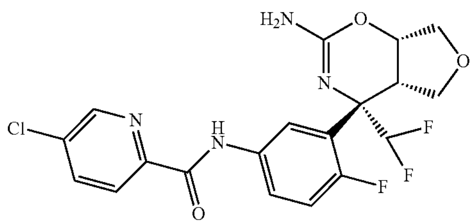 [SMILES: NC1=N[C@@](c2cc(NC(=O)c3ccc(Cl)cn3)ccc2F)(C(F)F)[C@H]2COC[C@H]2O1] | 0.0055 | — |
| 17 | 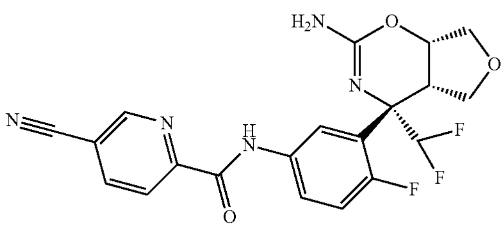 [SMILES: N#Cc1ccc(C(=O)Nc2ccc(F)c([C@@]3(C(F)F)N=C(N)O[C@@H]4COC[C@@H]43)c2)nc1] | 0.006 | — |
| 18 | 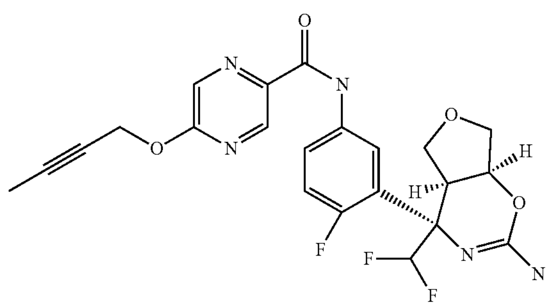 [SMILES: CC#CCOc1cnc(C(=O)Nc2ccc(F)c([C@@]3(C(F)F)N=C(N)O[C@@H]4COC[C@@H]43)c2)cn1] | — | — |
| 19 | rac | 0.009 | — |
| 20 | rac | 0.007 | — |

TABLE 1-continued

IC$_{50}$ values of selected examples

| Exam. | Structure | BACE1 IC$_{50}$ [μM] | BACE2 IC$_{50}$ [μM] |
|---|---|---|---|
| 21 | 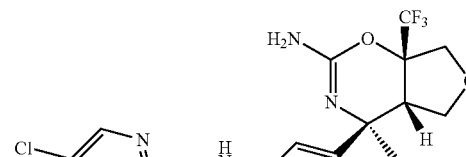 | 0.034 | — |
| 22 | 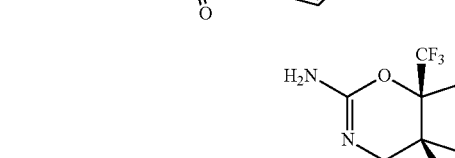 | 0.007 | — |

Pharmaceutical Compositions

The compounds of formula I and their pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention provides pharmaceutical compositions containing a compound of formula I or a pharmaceutically acceptable salt thereof and a therapeutically inert carrier, as is a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, preferably 1-100 mg, of a compound of formula I. Examples of compositions according to the invention are:

Example A

Tablets of the following composition are manufactured in the usual manner:

TABLE 2 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Example B-1

Capsules of the following composition are manufactured:

TABLE 3 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Example B-2

Soft Gelatin Capsules of the following composition are manufactured:

TABLE 4 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 5 possible soft gelatin capsule composition

| ingredient | mg/capsule |
|---|---|
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure
The compound of formula I is dissolved in a warm melting of the other ingredients and the mixture is filled into soft gelatin capsules of appropriate size. The filled soft gelatin capsules are treated according to the usual procedures.

Example C

Suppositories of the following composition are manufactured:

TABLE 6 possible suppository composition

| ingredient | mg/supp. |
|---|---|
| Compound of formula I | 15 |
| Suppository mass | 1285 |
| Total | 1300 |

Manufacturing Procedure
The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

Example D

Injection solutions of the following composition are manufactured:

TABLE 7 possible injection solution composition

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

Manufacturing Procedure
The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

Example E

Sachets of the following composition are manufactured:

TABLE 8 possible sachet composition

| ingredient | mg/sachet |
|---|---|
| Compound of formula I | 50 |
| Lactose, fine powder | 1015 |
| Microcrystalline cellulose (AVICEL PH 102) | 1400 |
| Sodium carboxymethyl cellulose | 14 |

TABLE 8-continued

| possible sachet composition | |
|---|---|
| ingredient | mg/sachet |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

EXPERIMENTAL PART

The following examples are provided for illustration of the invention. They should not be considered as limiting the scope of the invention, but merely as being representative thereof.

General Procedure A: Synthesis of the Intermediate Dihydroisoxazole IV

To a stirred solution of the nitro compound II (72.8 mmol) and the olefine III (71.3 mmol) in benzene (105 ml) was added triethylamine (NEt$_3$) (10 drops) followed by the addition of a solution of phenylisocyanate (146 mmol) in benzene (15 ml) and stirring was continued at 22° C. for 1 h and at reflux temperature for 1 h. Alternatively, diethylether can be used as solvent and the reaction mixture was stirred at 22° C. for 3 days. The suspension was filtered and the filtrate was chromatographed on silica using a mixture of cyclohexane and ethyl acetate (AcOEt) to afford the pure dihydroisoxazole IV.

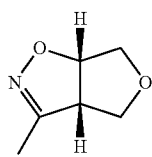

rac

Intermediate IV-1: Starting from nitroethane and 2,5-dihydro-furan, the product (3aS,6aS)-rel-3-methyl-3a,4,6,6a-tetrahydro-furo[3,4-d]isoxazole was obtained as a pale yellow solid.

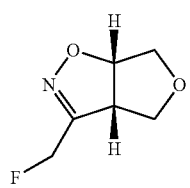

rac

Intermediate IV-2: A solution of (3aS,6aS)-rel-1-(3a,4,6,6a-tetrahydro-furo[3,4-d]isoxazol-3-yl)-methanol (14.0 mmol) in dichloromethane (40 ml) was treated dropwise with a solution of (diethylamino)sulfur trifluoride (15.4 mmol) in dichloromethane (5 ml) at −70° C. The colorless turbid solution was stirred at −70° C. for 30 minutes and then allowed to warm to room temperature while its color turned to brown. After stirring for one hour the dark brown solution was cooled in an ice-bath and quenched with a saturated solution of sodium hydrogencarbonate (50 ml). The aqueous layer was separated and extracted twice with dichloromethane. The combined organic layers were dried over sodium sulphate, then evaporated. The crude product was purified by chromatography on silica gel using a gradient of heptane and ethyl acetate=100:0 to 80:20 as the eluent. The (3aS,6aS)-rel-3-fluoromethyl-3a,4,6,6a-tetrahydro-furo[3,4-d]isoxazole (814 mg, 40% yield) was obtained as a light yellow solid. MS: m/z=146.2 [M+H]$^+$.

The (3aS,6aS)-rel-1-(3a,4,6,6a-tetrahydro-furo[3,4-d]isoxazol-3-yl)-methanol was obtained as follows:

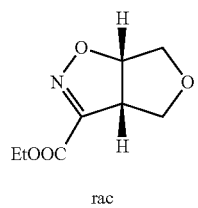 [SMILES: CCOC(=O)C1=NO[C@@H]2COC[C@H]12]

rac

Starting from commercially available (Z)-ethyl 2-chloro-2-(hydroxyimino)acetatenitroethane and 2,5-dihydro-furan following general procedure A, the product (3aS,6aS)-rel-3a,4,6,6a-tetrahydro-furo[3,4-d]isoxazole-3-carboxylic acid ethyl ester was obtained as a yellow liquid.

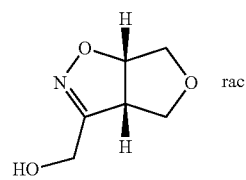

rac

A solution of (3aS,6aS)-rel-3a,4,6,6a-tetrahydro-furo[3,4-d]isoxazole-3-carboxylic acid ethyl ester (18.9 mmol) (intermediate IV-2) in ethanol (60 ml) was cooled to 5° C. Sodium borohydride (37.8 mmol) was added portionwise over a period of 15 minutes. During gas evolution the temperature was maintained between 5 and 10° C. Thereafter, the reaction mixture was stirred between 25 and 28° C. for 1 hour. For the workup, the reaction mixture was cooled in an ice bath and 3M hydrochloric acid (12 ml) was added dropwise. The mixture was allowed to warm to room temperature and was then treated with a solution sodium carbonate (2M; 10 ml). The suspension was concentrated at reduced pressure, the resulting solid was stirred in dichloromethane, then filtered, and the filtrate was concentrated at reduced pressure. The crude product was purified by chromatography on silica gel using a gradient of heptane and ethyl acetate=100:0 to 0:100 as the eluent. The (3aS,6aS)-rel-1-(3a,4,6,6a-tetrahydro-furo[3,4-d]isoxazol-3-yl)-methanol (2.06 g, 76% yield) was obtained as a light yellow oil. MS: m/z=144.0 [M+H]$^+$.

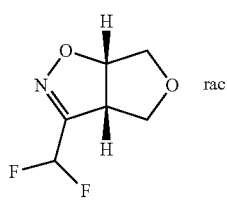

Intermediate IV-3: A solution of (3aS,6aS)-rel-3a,4,6,6a-tetrahydro-furo[3,4-d]isoxazole-3-carbaldehyde (35.4 mmol) in dichloromethane (20 ml) was treated dropwise with (diethylamino)sulfur trifluoride (42.5 mmol) at −2° C. The reaction mixture was stirred at 0° C. for 2 hours. For the workup, the reaction mixture was carefully quenched dropwise with a saturated solution of sodium hydrogencarbonate (25 ml), thereafter a solution of sodium carbonate (10%) was added to adjust to an alkaline pH. The mixture was extracted three times with dichloromethane, the organic layers were combined, dried over sodium sulphate and evaporated. For purification, the crude product was distilled at reduced pressure. The (3aS,6aS)-rel-3-difluoromethyl-3a,4,6,6a-tetrahydro-furo[3,4-d]isoxazole (2.9 g, 50% yield) was obtained as a light yellow oil.

The (3aS,6aS)-rel-3a,4,6,6a-tetrahydro-furo[3,4-d]isoxazole-3-carbaldehyde was obtained as follows:

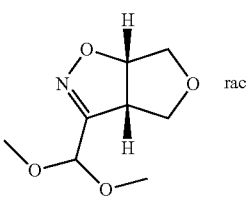

Starting from the commercially available 1,1-dimethoxy-2-nitroethane (CAS69425-53-2) and 2,5-dihydro-furan following general procedure A, the product (3aS,6aS)-rel-3-dimethoxymethyl-3a,4,6,6a-tetrahydro-furo[3,4-d]isoxazole was obtained as a light brown oil.

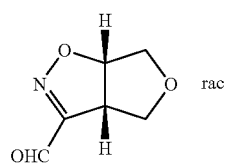

A solution of (3aS,6aS)-rel-3-dimethoxymethyl-3a,4,6,6a-tetrahydro-furo[3,4-d]isoxazole (35.3 mmol) in trifluoroacetic acid (30 ml) was treated with water (1.3 ml). The mixture was stirred at room temperature for 30 minutes. For the workup, the reaction mixture was diluted with water (100 ml) and extracted three times with dichloromethane. The combined organic layers were dried over sodium sulphate and evaporated. The crude product was purified by chromatography on silica gel using a 5:1-mixture of dichloromethane and heptane as the eluent. The (3aS,6aS)-rel-3a,4,6,6a-tetrahydro-furo[3,4-d]isoxazole-3-carbaldehyde (4.79 g, 96% yield) was obtained as a yellow oil. MS: m/z=144.0 [M+H]$^+$.

General Procedure B: Synthesis of the Intermediate Isoxazolidine VI and VII

To a stirred solution of the arylbromide V (8.26 mmol) in THF (5 ml) and toluene (15 ml) was added at −78° C. n-BuLi (1.6 M in hexane, 4.9 ml) over 10 min and stirring was continued at −78° C. for 1 h.

To a solution of the dihydroisoxazole IV (3.9 mmol) in toluene (35 ml) was added at −78° C. boron trifluoride etherate (BF$_3$.Et$_2$O) (7.9 mmol) which followed by the addition of the phenyllithium reagent prepared above using an insulated cannula over 10 min keeping the temperature below −70° C. The mixture was stirred at −78° C. for 1 h, quenched with saturated aqueous ammonium chloride (NH$_4$Cl) and extracted with AcOEt. The organic layer was washed with brine, dried, evaporated and the residue was chromatographed on silica using a mixture of cyclohexane and AcOEt to afford the pure isoxazolidine VI.

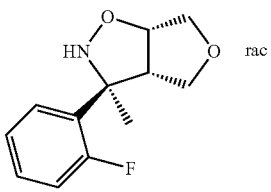

Intermediate VI-1: Starting from (3aS,6aS)-rel-3-methyl-3a,4,6,6a-tetrahydro-furo[3,4-d]isoxazole, the product (3S,3aS,6aS)-rel-3-(2-fluorophenyl)-3-methylhexahydrofuro[3,4-d]isoxazole was obtained as an off-white solid. MS: m/z=224.2 [M+H]$^+$.

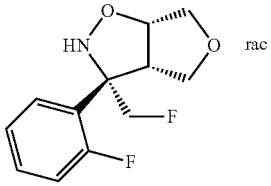

Intermediate VI-2: Starting from (3aS,6aS)-rel-3-fluoromethyl-3a,4,6,6a-tetrahydro-furo[3,4-d]isoxazole and 1-bromo-2-fluorobenzene, the product (3S,3aS,6aS)-rel-3-fluoromethyl-3-(2-fluoro-phenyl)-hexahydro-furo[3,4-d]isoxazole was obtained as a light yellow oil. MS: m/z=242.1 [M+H]$^+$.

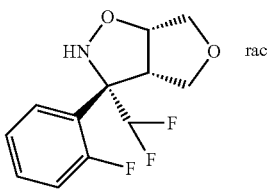

Intermediate VI-3: Starting from (3aS,6aS)-rel-3-difluoromethyl-3a,4,6,6a-tetrahydro-furo[3,4-d]isoxazole and 1-bromo-2-fluorobenzene, the product (3S,3aS,6aS)-rel-3-difluoromethyl-3-(2-fluorophenyl)-hexahydro-furo[3,4-d]isoxazole was obtained as an orange oil. MS: m/z=260.2 [M+H]$^+$.

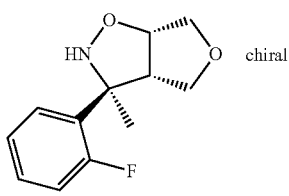

Intermediate VII-1: The racemate of (3S,3aS,6aS)-3-(2-fluorophenyl)-3-methylhexahydrofuro[3,4-d]isoxazole was resolved on a chiral high-performance liquid chromatography (HPLC) column (Chiralpack AD) using n-heptane/ethanol (85:15) to give the desired (3S,3aS,6aS)-3-(2-fluorophenyl)-3-methylhexahydrofuro[3,4-d]isoxazole as the faster eluting enantiomer and (3R,3aR,6aR)-3-(2-fluoro-phenyl)-3-methyl-hexahydro-furo[3,4-d]isoxazole as the slower eluting enantiomer.

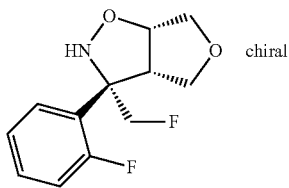

Intermediate VII-2: The racemate of (3S,3aS,6aS)-3-fluoromethyl-3-(2-fluorophenyl)-hexahydro-furo[3,4-d]isoxazole was resolved on a chiral high-performance liquid chromatography (HPLC) column (Chiralpack AD) using n-heptane/ethanol (85:15) to give the desired (3S,3aS,6aS)-3-fluoromethyl-3-(2-fluoro-phenyl)-hexahydro-furo[3,4-d]isoxazole as the faster eluting enantiomer and (3R,3aR,6aR)-3-fluoromethyl-3-(2-fluoro-phenyl)-hexahydro-furo[3,4-d]isoxazole as the slower eluting enantiomer.

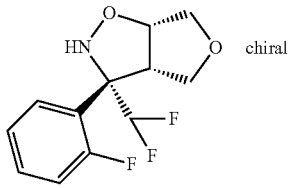

Intermediate VII-3: The racemate of (3S,3aS,6aS)-3-difluoromethyl-3-(2-fluorophenyl)-hexahydro-furo[3,4-d]isoxazole was resolved on a chiral high-performance liquid chromatography (HPLC) column (Chiralpack AD) using n-heptane/isopropanol to give the desired (3S,3aS,6aS)-3-difluoromethyl-3-(2-fluorophenyl)-hexahydrofuro[3,4-d]isoxazole as the second eluting enantiomer and (3R,3aR,6aR)-3-difluoromethyl-3-(2-fluoro-phenyl)-hexahydro-furo[3,4-d]isoxazole as the first eluting enantiomer.

General Procedure C: Synthesis of the Intermediate Aminoalcohol VIII

To a solution of the isoxazolidine VII (6.4 mmol) in EtOH (40 ml) was added Pd/C (10%, 288 mg) and ammonium formate (3.2 g) and stirring of the mixture was continued at 22° C. for 3 h. The suspension was filtered, the filtrate evaporated and the residue was partitioned between AcOEt and saturated aqueous Sodium hydrogen carbonate (NaHCO₃) solution. The organic layer was dried, evaporated and the residue was chromatographed on a Si—NH₂ column using a mixture of cyclohexane and AcOEt to afford the pure amino alcohol VIII.

Intermediate VIII-1: Starting from (3S,3aS,6aS)-3-(2-fluorophenyl)-3-methylhexahydrofuro[3,4-d]isoxazole, the product (3S,4S)-4-[(S)-1-amino-1-(2-fluoro-phenyl)-ethyl]-tetrahydro-furan-3-ol was obtained as a colorless oil. MS: m/z=226.2 [M+H]⁺.

Intermediate VIII-2: Starting from (3S,3aS,6aS)-3-fluoromethyl-3-(2-fluoro-phenyl)-hexahydro-furo[3,4-d]isoxazole, the product (3S,4S)-4-[(S)-1-amino-2-fluoro-1-(2-fluoro-phenyl)-ethyl]-tetrahydro-furan-3-ol was obtained as a white solid. MS: m/z=244.2 [M+H]⁺.

Intermediate VIII-3: Starting from (3S,3aS,6aS)-3-difluoromethyl-3-(2-fluoro-phenyl)-hexahydro-furo[3,4-d]isoxazole, the product (3S,4S)-4-[(S)-1-amino-2,2-difluoro-1-(2-fluoro-phenyl)-ethyl]-tetrahydro-furan-3-ol was obtained as a colorless solid. MS: m/z=262.2 [M+H]⁺.

General Procedure D: Synthesis of the Intermediate Oxazine IX

To a solution of the aminoalcohol VIII (5.9 mmol) in THF (130 ml) was added subsequently sodium acetate (6.8 mmol) and a solution of cyanobromide (Br—CN) (5M in acetonitrile (CH₃CN), 6.8 mmol) and the mixture was stirred at reflux temperature for 16 h. The mixture was diluted with hydrochloric acid (HCl) in 1,4-dioxane (4 M, 7.1 ml) and stirring was continued at 22° C. for 1 h. The mixture was partitioned between AcOEt and saturated aqueous sodium carbonate (Na₂CO₃) solution, the organic layer was dried, evaporated and the residue was chromatographed on silica using a mixture of AcOEt and methanol (MeOH) (9:1) to afford the pure oxazine IX.

Intermediate IX-1: Starting from (3S,4S)-4-[(S)-1-amino-1-(2-fluoro-phenyl)-ethyl]-tetrahydro-3-ol, the product (3aS,7S,7aS)-7-(2-fluoro-phenyl)-7-methyl-3,3a,7,7a-tetrahydro-1H-2,4-dioxa-6-aza-inden-5-ylamine was obtained as a pale yellow amorphous solid. MS: m/z=251.1 [M+H]⁺.

Intermediate IX-2: Starting from (3S,4S)-4-[(S)-1-amino-2-fluoro-1-(2-fluoro-phenyl)-ethyl]-tetrahydro-furan-3-ol, the product (3aS,7S,7aS)-7-fluoromethyl-7-(2-fluoro-phenyl)-3,3a,7,7a-tetrahydro-1H-2,4-dioxa-6-aza-inden-5-ylamine was obtained as a white foam. MS: m/z=269.1 [M+H]⁺.

Intermediate IX-3: Starting from (3S,4S)-4-[(S)-1-amino-2,2-difluoro-1-(2-fluoro-phenyl)-ethyl]-tetrahydro-furan-3-ol, the product (3aS,7S,7aS)-7-difluoromethyl-7-(2-fluoro-phenyl)-3,3a,7,7a-tetrahydro-1H-2,4-dioxa-6-aza-inden-5-ylamine was obtained as a colorless solid. MS: m/z=287.2 [M+H]⁺.

General Procedure E: Synthesis of the Intermediate Nitro-Oxazine X

To concentrated sulfuric acid (13 ml) was added portion wise the oxazine IX (3.0 mmol) at 22° C., the solution obtained was cooled to 0° C. and treated with red fuming nitric acid (HNO₃) (0.19 ml) over 20 min and stirring was continued at 0° C. for 1 h. The reaction mixture was slowly added to crushed ice (60 g), the pH was adjusted to 10 using sodium hydroxide (NaOH), the aqueous layer was extracted with AcOEt, the organic layer was dried, evaporated and the residue was chromatographed on silica using a mixture of AcOEt/MeOH (9:1) to afford the pure nitro-oxazine X.

Intermediate X-1: Starting from (3aS,7S,7aS)-7-(2-fluoro-phenyl)-7-methyl-3,3a,7,7a-tetrahydro-1H-2,4-dioxa-6-aza-inden-5-ylamine, the product (3aS,7S,7aS)-7-(2-fluoro-5-nitro-phenyl)-7-methyl-3,3a,7,7a-tetrahydro-1H-2,4-dioxa-6-aza-inden-5-ylamine was obtained as a pale yellow amorphous solid. MS: m/z=296.2 [M+H]⁺.

Intermediate X-2: Starting from (3aS,7S,7aS)-7-fluoromethyl-7-(2-fluoro-phenyl)-3,3a,7,7a-tetrahydro-1H-2,4-dioxa-6-aza-inden-5-ylamine, the product (3aS,7S,7aS)-7-fluoromethyl-7-(2-fluoro-5-nitro-phenyl)-3,3a,7,7a-tetrahydro-1H-2,4-dioxa-6-aza-inden-5-ylamine was obtained as a white solid. MS: m/z=313.9 [M+H]$^+$.

Intermediate X-3: Starting from (3aS,7S,7aS)-7-difluoromethyl-7-(2-fluoro-phenyl)-3,3a,7,7a-tetrahydro-1H-2,4-dioxa-6-aza-inden-5-ylamine, the product (3aS,7S,7aS)-7-difluoromethyl-7-(2-fluoro-5-nitro-phenyl)-3,3a,7,7a-tetrahydro-1H-2,4-dioxa-6-aza-inden-5-ylamine was obtained as a light yellow solid. MS: m/z=332.2 [M+H]$^+$.

General Procedure F: Synthesis of the Intermediate Aniline XI

A suspension of the nitro-oxazine X (2.6 mmol) in EtOH (40 ml) and NEt$_3$ (0.2 ml) was treated with Pd/C (10%, 80 mg) and the mixture was hydrogenated at atmospheric pressure and 22° C. for 2 h. The mixture was filtered, the filtrated evaporated and the residue was chromatographed on a Si—NH$_2$ column using a mixture of AcOEt/MeOH (9:1) to afford the pure aniline XI.

Intermediate XI-1: Starting from (3aS,7S,7aS)-7-(2-fluoro-phenyl)-7-methyl-3,3a,7,7a-tetrahydro-1H-2,4-dioxa-6-aza-inden-5-ylamine, the (3aS,7S,7aS)-7-(5-amino-2-fluoro-phenyl)-7-methyl-3,3a,7,7a-tetrahydro-1H-2,4-dioxa-6-aza-inden-5-ylamine was obtained as a white amorphous solid. MS: m/z=266.1 [M+H]$^+$.

Intermediate XI-2: Starting from (3aS,7S,7aS)-7-fluoromethyl-7-(2-fluoro-5-nitro-phenyl)-3,3a,7,7a-tetrahydro-1H-2,4-dioxa-6-aza-inden-5-ylamine, the (3aS,7S,7aS)-7-fluoromethyl-7-(5-amino-2-fluoro-5-phenyl)-3,3a,7,7a-tetrahydro-1H-2,4-dioxa-6-aza-inden-5-ylamine was obtained as a white foam. MS: m/z=284.1 [M+H]$^+$.

Intermediate XI-3: Starting from (3aS,7S,7aS)-7-difluoromethyl-7-(2-fluoro-5-nitro-phenyl)-3,3a,7,7a-tetrahydro-1H-2,4-dioxa-6-aza-inden-5-ylamine, the (3aS,7S,7aS)-7-difluoromethyl-7-(5-amino-2-fluoro-5-phenyl)-3,3a,7,7a-tetrahydro-1H-2,4-dioxa-6-aza-inden-5-ylamine was obtained as a colorless foam. MS: m/z=302.3 [M+H]$^+$.

General Procedure G: Synthesis of the Intermediate O-Protected Aminoalcohol XIIIb

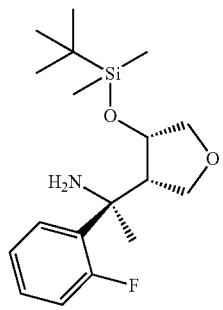 [SMILES: CC(C)(C)[Si](C)(C)O[C@@H]1COC[C@@H]1[C@](C)(N)c1ccccc1F]

A solution of the aminoalcohol VIIIb (13.9 mmol) in dichloromethane (91 ml) was treated at 0° C. with triethylamine (4.48 g, 44.3 mmol) and 4-(dimethylamino)-pyridine (846 mg, 6.93 mmol), followed by tert-butyldimethylchlorosilane (4.18 g, 27.7 mmol). The reaction mixture was left to warm to room temperature and stirred overnight. Dilution with dichloromethane and extraction of the reaction mixture with a saturated solution of sodium hydrogencarbonate NaHCO3, separation of the organic layer, drying over sodium sulphate and evaporation yielded the crude product which was purified by chromatography on silica gel using a gradient of heptane and ethyl acetate=100:0 to 0:100 as the eluent.

Intermediate XIIIb-1: Starting from rel-(3S,4S)-4-((S)-1-amino-1-(2-fluorophenyl)ethyl)tetrahydrofuran-3-ol), the rel-(S)-1-((3S,4S)-4-(tert-butyldimethylsilyloxy)tetrahydrofuran-3-yl)-1-(2-fluorophenyl)ethanamine was obtained as a colorless oil.

Intermediate XIIIb-2: Starting from (3S,4S)-4-((S)-1-amino-1-(2-fluorophenyl)ethyl)tetrahydrofuran-3-ol), the (S)-1-((3S,4S)-4-(tert-butyldimethylsilyloxy)tetrahydrofuran-3-yl)-1-(2-fluorophenyl)ethanamine was obtained as a colorless oil. MS: m/z=340.3 [M+H]$^+$.

General Procedure H: Synthesis of the Intermediate Diprotected Aminoalcohol XIVb A solution of the protected aminoalcohol XIIIb (19.1 mmol) and triethylamine (2.9 g, 28.6 mmol) in dichloromethane (34 ml) was treated dropwise at 0° C. with tert-butylsulfinyl chloride (2.95 g, 21.0 mmol). The reaction was stirred at 0° C. for 3 hours. In order to complete the reaction, tert-butylsulfinyl chloride (0.5 ml, 4 mmol) was added again and the reaction mixture stirred for 20 minutes at 0° C. For the workup, the reaction mixture was diluted with dichloromethane and extracted with a saturated solution of sodium hydrogencarbonate NaHCO3. The organic layer was separated and dried over sodium sulphate. Evaporation yielded the crude product which was purified by chromatography on silica gel using a gradient of heptane and ethyl acetate=100:0 to 0:100 as the eluent.

Intermediate XIVb-1: Starting from rel-(S)-1-((3S,4S)-4-(tert-butyldimethylsilyloxy)tetrahydrofuran-3-yl)-1-(2-fluorophenyl)ethanamine, the (R)—N-rel-((S)-1-((3S,4S)-4-(tert-butyldimethylsilyloxy)tetrahydrofuran-3-yl)-1-(2-fluorophenyl)ethyl)-2-methylpropane-2-sulfinamide and the (S)—N-rel-((S)-1-((3S,4S)-4-(tert-butyldimethylsilyloxy)tetrahydrofuran-3-yl)-1-(2-fluorophenyl)ethyl)-2-methylpropane-2-sulfinamide were obtained both as colorless oils.

Intermediate XIVb-2: Starting from (S)-1-((3S,4S)-4-(tert-butyldimethylsilyloxy)tetrahydrofuran-3-yl)-1-(2-fluorophenyl)ethanamine, the (R)—N—((S)-1-((3S,4S)-4-(tert-butyldimethylsilyloxy)tetrahydrofuran-3-yl)-1-(2-fluorophenyl)ethyl)-2-methylpropane-2-sulfinamide and the (S)—N—((S)-1-((3S,4S)-4-(tert-butyldimethylsilyloxy)tetrahydrofuran-3-yl)-1-(2-fluorophenyl)ethyl)-2-methylpropane-2-sulfinamide were obtained both as colorless oils.

General Procedure I: Synthesis of the Intermediate N-Protected Aminoalcohol XVb

A solution of the diprotected aminoalcohol XIVb (5.43 mmol) in tetrahydrofuran (7 ml) was treated at 23° C. with tetrabutylammonium fluoride (1 M in tetrahydrofuran) (7.0 ml, 7.00 mmol) and stirred for 45 minutes. For the workup, the reaction mixture was poured into a saturated solution of ammonium chloride, then extracted with ethyl acetate. The organic layer was separated and washed with brine. The combined aqueous layers were re-extracted with ethyl acetate, and the combined organic layers were dried over sodium sulphate and evaporated at reduced pressure. The crude product was purified by chromatography on silica gel using a gradient of heptane and ethyl acetate=100:0 to 0:100 as the eluent.

Intermediate XVb-1: Starting from (S or R)—N-rel-((S)-1-((3S,4S)-4-(tert-butyldimethylsilyloxy)tetrahydrofuran-3-yl)-1-(2-fluorophenyl)ethyl)-2-methylpropane-2-sulfinamide, the (S or R)—N-rel-((SR)-1-(2-fluorophenyl)-1-((3S,4S)-4-hydroxytetrahydrofuran-3-yl)ethyl)-2-methylpropane-2-sulfinamide was obtained as a white solid.

Intermediate XVb-2: Starting from (S or R)—N—((S)-1-((3S,4S)-4-(tert-butyldimethylsilyloxy)tetrahydrofuran-3-yl)-1-(2-fluorophenyl)ethyl)-2-methylpropane-2-sulfinamide, the (S or R)—N—((S)-1-(2-fluorophenyl)-1-((3S,4S)-4-hydroxytetrahydrofuran-3-yl)ethyl)-2-methylpropane-2-sulfinamide was obtained as an off-white solid. MS: m/z=330.1 [M+H]$^+$.

General Procedure J: Synthesis of the Intermediate Ketone XVIb

Under a dry atmosphere of argon oxalyl chloride (896 mg, 7.06 mmol) was dissolved in dry dichloromethane (16.5 ml). At −78° C. dry dimethylsulfoxide (1.00 ml, 14.1 mmol) was added dropwise via syringe. The resulting mixture was stirred for 15 minutes, thereafter, the fine suspension of the N-protected aminoalcohol XVb (4.71 mmol) in dry dichloromethane (19 ml) was added via syringe. The mixture was stirred at −78° C. for 30 minutes. Then triethylamine (3.28 ml, 23.5 mmol) was added, and the resultant mixture was stirred at −78° C. for 10 minutes then between −78° C. and 10° C. For the workup, the reaction was quenched with a solution of ammonium chloride (20 ml), diluted with dichloromethane, extracted with citric acid (pH=2-3), washed with a solution of sodium hydrogencarbonate and brine. The organic layer was dried over sodium sulphate and evaporated. The crude product was purified by chromatography on silica gel using a gradient of heptane and ethyl acetate=100:0 to 20:80 as the eluent.

Intermediate XVIb-1: Starting from (S or R)—N-rel-((S)-1-(2-fluorophenyl)-1-((3S,4S)-4-hydroxytetrahydrofuran-3-yl)ethyl)-2-methylpropane-2-sulfinamide, the (S or R)—N-rel-((S)-1-(2-fluorophenyl)-1-((S)-4-oxotetrahydrofuran-3-yl)ethyl)-2-methylpropane-2-sulfinamide was obtained as a light yellow oil. MS: m/z=328.2 [M+H]$^+$.

Intermediate XVIb-2: Starting from (S or R)—N—((S)-1-(2-fluorophenyl)-1-((3S,4S)-4-hydroxytetrahydrofuran-3-yl)ethyl)-2-methylpropane-2-sulfinamide, the (S or R)—N—((S)-1-(2-fluorophenyl)-1-((S)-4-oxotetrahydrofuran-3-yl)ethyl)-2-methylpropane-2-sulfinamide was obtained as a light yellow oil. MS: m/z=328.2 [M+H]$^+$.

General Procedure K: Synthesis of the Intermediate Trifluoromethyl Derivative XVIIb A solution of the intermediate ketone XVIb (2.72 mmol) in tetrahydrofuran (15 ml) was treated dropwise at 0° C. with (trifluoromethyl)trimethylsilane (580 mg, 603 μl, 4.08 mmol). Thereafter, at 0° C. tetrabutylammonium fluoride (1 M in tetrahydrofuran) (136 μl, 136 μmol) was added. The brown solution was left to warm to room temperature and stirred for 3 hours. In order to complete the reaction, tetrabutylammonium fluoride (1 M in tetrahydrofuran) (4.08 ml, 4.08 mmol) was added and stirring continued for 1 hour. For the workup, the reaction mixture was quenched with water, the aqueous layer extracted with ethyl acetate, the organic layer washed with brine and dried over sodium sulphate. After evaporation at reduced pressure the residue was purified by chromatography on silica gel using a gradient of heptane and ethyl acetate=100:0 to 0:100 as the eluent.

Intermediate XVIIb-1: Starting from (S or R)—N-rel-(S)-1-(2-fluorophenyl)-1-(S)-4-oxotetrahydrofuran-3-yl)ethyl)-2-methylpropane-2-sulfinamide, the (S or R)—N-rel-((S)-1-(2-fluorophenyl)-1-((3S,4S)-4-hydroxy-4-(trifluoromethyl)tetrahydrofuran-3-yl)ethyl)-2-methylpropane-2-sulfinamide was obtained as a light brown solid. MS: m/z=398.1 [M+H]$^+$.

Intermediate XVIIb-2: Starting from (S or R)—N—((S)-1-(2-fluorophenyl)-1-((S)-4-oxotetrahydrofuran-3-yl)ethyl)-2-methylpropane-2-sulfinamide, the (S or R)—N—((S)-1-(2-fluorophenyl)-1-((3S,4S)-4-hydroxy-4-(trifluoromethyl)tetrahydrofuran-3-yl)ethyl)-2-methylpropane-2-sulfinamide was obtained as a light brown foam. MS: m/z=398.1 [M+H]$^+$.

General Procedure L: Synthesis of the Intermediate Aminoalcohol XVIIIb

A solution of the intermediate trifluoromethyl derivative XVIIb (1.4 mmol) in tetrahydrofuran (15 ml) was treated at 23° C. with hydrochloric acid (37% in water) (573 μl, 6.98 mmol). The yellow solution was stirred at 23° C. for 2 hours, then poured into a solution of sodium carbonate (1 M). The mixture was extracted twice with ethyl acetate, the combined organic layers were dried over sodium sulphate and evaporated at reduced pressure. The combined organic layers were dried over Na2SO4, filtered and evaporated. The crude product was purified by chromatography on silica gel using a gradient of heptane and ethyl acetate=100:0 to 50:50 as the eluent.

Intermediate XVIIIb-1: Starting from (S or R)—N-rel-((S)-1-(2-fluorophenyl)-1-((3S,4S)-4-hydroxy-4-(trifluoromethyl)tetrahydrofuran-3-yl)ethyl)-2-methylpropane-2-sulfinamide, the rel-(3S,4S)-4-((S)-1-amino-1-(2-fluorophenyl)ethyl)-3-(trifluoromethyl)tetrahydrofuran-3-ol was obtained as a light yellow oil. MS: m/z=294.1 [M+H]$^+$.

Intermediate XVIIIb-2: Starting from (S or R)—N—((S)-1-(2-fluorophenyl)-1-((3S,4S)-4-hydroxy-4-(trifluoromethyl)tetrahydrofuran-3-yl)ethyl)-2-methylpropane-2-sulfinamide, the (3S,4S)-4-((S)-1-amino-1-(2-fluorophenyl)ethyl)-3-(trifluoromethyl)tetrahydrofuran-3-ol was obtained as a brown oil. MS: m/z=294.2 [M+H]$^+$.

General Procedure M: Synthesis of the Intermediate O-Protected Aminoalcohol XIXb Sodium hydride (55% dispersion in oil) (116 mg, 2.67 mmol) was added at 0° C. to a solution of the aminoalcohol XVIIIb (1.48 mmol, Eq: 1.00) in N,N-dimethylformamide (6 ml). After stirring for 30 minutes at 23° C. the reaction mixture was treated at 0° C. with tert-butyldimethylsilyltrifluoromethanesulfonate (728 mg, 632 μl, 2.67 mmol). After stirring for 16 hours, the reaction mixture was extracted with a mixture of dichloromethane and a saturated solution of sodium hydrogencarbonate. The organic layer was separated, dried over sodium sulphate and evaporated. The residue was purified by chromatography on silica gel using a gradient of heptane and ethyl acetate=100:0 to 50:50 as the eluent.

Intermediate XIXb-1: Starting from rel-(3S,4S)-4-((S)-1-amino-1-(2-fluorophenyl)ethyl)-3-(trifluoromethyl)tetrahydrofuran-3-ol, the rel-(S)-1-((3S,4S)-4-(tert-butyldimethylsilyloxy)-4-(trifluoromethyl)tetrahydrofuran-3-yl)-1-(2-fluorophenyl)ethanamine was obtained as a colorless oil.

Intermediate XIXb-2: Starting from (3S,4S)-4-((S)-1-amino-1-(2-fluorophenyl)ethyl)-3-(trifluoromethyl)tetrahydrofuran-3-ol, the (S)-1-((3S,4S)-4-(tert-butyldimethylsilyloxy)-4-(trifluoromethyl)tetrahydrofuran-3-yl)-1-(2-fluorophenyl)ethanamine was obtained as a light yellow oil. MS: m/z=408.3 [M+H]$^+$.

General Procedure N: Synthesis of the Intermediate Isothiocyanate XXb

A mixture of the O-protected aminoalcohol XIXb (908 μmol) and sodium bicarbonate (381 mg, 4.54 mmol) in dichloromethane (6 ml) was treated at 0° C. with thiophosgene (129 mg, 86.1 μl, 1.09 mmol). The reaction mixture was stirred at 23° C. for 4 hours. For the workup, the reaction mixture was extracted with a mixture of dichloromethane and water. The organic layer was separated, dried over sodium sulphate and evaporated. The crude product was engaged in the next step without further purification.

Intermediate XXb-1: Starting from rel-(S)-1-((3S,4S)-4-(tert-butyldimethylsilyloxy)-4-(trifluoromethyl)tetrahydrofuran-3-yl)-1-(2-fluorophenyl)ethanamine, the tert-butyl-rel- ((3S,4S)-4-((S)-1-(2-fluorophenyl)-1-isothiocyanatoethyl)-3-(trifluoromethyl)tetrahydrofuran-3-yloxy)dimethylsilane was obtained as a colorless oil.

Intermediate XXb-2: Starting from (S)-1-((3S,4S)-4-(tert-butyldimethylsilyloxy)-4-(trifluoromethyl)tetrahydrofuran-3-yl)-1-(2-fluorophenyl)ethanamine, the tert-butyl-((3S,4S)-4-((S)-1-(2-fluorophenyl)-1-isothiocyanatoethyl)-3-(trifluoromethyl)tetrahydrofuran-3-yloxy)dimethylsilane was obtained as a brown oil.

General Procedure O: Synthesis of the Intermediate N-Benzylated Oxazine XXIb

A solution of the isothiocyanate XXb (1.09 mmol) in acetonitrile (11 ml) was treated at room temperature with 2,4-dimethoxybenzylamine (273 mg, 246 µl, 1.63 mmol). The colorless solution was stirred at 70° C. for 16 hours. Tetrabutylammonium fluoride trihydrate (378 mg, 1.2 mmol) was added at 23° C. and stirring continued for 2 hours. Thereafter, 1-ethyl-3-(3-dimethylaminopropyl)carbodiimide (418 mg, 2.18 mmol) was added and stirring continued at 80° C. for 16 hours. For the workup, the reaction mixture was extracted with a mixture of ethyl acetate and a saturated solution of sodium hydrogencarbonate. The organic layer was separated, dried over sodium sulphate and evaporated. The crude product was purified by chromatography on silica gel using a gradient of heptane and ethyl acetate=100:0 to 65:35 as the eluent.

Intermediate XXIb-1: Starting from tert-butyl-rel-((3S,4S)-4-((S)-1-(2-fluorophenyl)-1-isothiocyanatoethyl)-3-(trifluoromethyl)tetrahydrofuran-3-yloxy)dimethylsilane, the rel-(4S,4aS,7aS)—N-(2,4-dimethoxybenzyl)-4-(2-fluorophenyl)-4-methyl-7a-(trifluoromethyl)-4a,5,7,7a-tetrahydro-4H-furo[3,4-e][1,3]oxazin-2-amine was obtained as a white solid. MS: m/z=469.23 [M+H]$^+$.

Intermediate XXIb-2: Starting from tert-butyl((3S,4S)-4-((S)-1-(2-fluorophenyl)-1-isothiocyanatoethyl)-3-(trifluoromethyl)tetrahydrofuran-3-yloxy)dimethylsilane, the (4S,4aS,7aS)—N-(2,4-dimethoxybenzyl)-4-(2-fluorophenyl)-4-methyl-7a-(trifluoromethyl)-4a,5,7,7a-tetrahydro-4H-furo[3,4-e][1,3]oxazin-2-amine was obtained as a colorless oil.

General Procedure P: Synthesis of the Intermediate Oxazine XXIIb

A solution of the N-benzylated oxazine XXIb (758 µmol) in trifluoroacetic acid (4.32 g, 2.92 ml, 37.9 mmol) was stirred for 5 hours. Trifluoromethanesulfonic acid (341 mg, 202 µl, 2.27 mmol) was added and stirring continued for another 2 hours. The dark red solution was poured into a solution of sodium carbonate (1 M) and extracted twice with dichloromethane. The combined organic layers were dried over sodium sulphate and evaporated. The crude product was purified by chromatography on silica gel using a 19:1-mixture of heptane and methanol as the eluent.

Intermediate XXIIb-1: Starting from rel-(4S,4aS,7aS)—N-(2,4-dimethoxybenzyl)-4-(2-fluorophenyl)-4-methyl-7a-(trifluoromethyl)-4a,5,7,7a-tetrahydro-4H-furo[3,4-e][1,3]oxazin-2-amine, the rel-(4S,4aS,7aS)-4-(2-fluorophenyl)-4-methyl-7a-(trifluoromethyl)-4a,5,7,7a-tetrahydro-4H-furo[3,4-e][1,3]oxazin-2-amine was obtained as a white solid. MS: m/z=319.0 [M+H]$^+$.

Intermediate XXIIb-2: Starting from (4S,4aS,7aS)—N-(2,4-dimethoxybenzyl)-4-(2-fluorophenyl)-4-methyl-7a-(trifluoromethyl)-4a,5,7,7a-tetrahydro-4H-furo[3,4-e][1,3]oxazin-2-amine, the (4S,4aS,7aS)-4-(2-fluorophenyl)-4-methyl-7a-(trifluoromethyl)-4a,5,7,7a-tetrahydro-4H-furo[3,4-e][1,3]oxazin-2-amine was obtained as a white gum. MS: m/z=319.0 [M+H]$^+$.

Synthesis of the Intermediate Nitro Oxazine XXIIIb

Intermediate XXIIIb-1: Following the General Procedure E, the nitration of rel-(4S,4aS,7aS)-4-(2-fluorophenyl)-4-methyl-7a-(trifluoromethyl)-4a,5,7,7a-tetrahydro-4H-furo[3,4-e][1,3]oxazin-2-amine yielded the rel-(4S,4aS,7aS)-4-(2-fluoro-5-nitrophenyl)-4-methyl-7a-(trifluoromethyl)-4a,5,7,7a-tetrahydro-4H-furo[3,4-e][1,3]oxazin-2-amine as a light brown solid. MS: m/z=364.0 [M+H]$^+$.

Intermediate XXIIIb-2: Following the General Procedure E, the nitration of (4S,4aS,7aS)-4-(2-fluorophenyl)-4-methyl-7a-(trifluoromethyl)-4a,5,7,7a-tetrahydro-4H-furo[3,4-e][1,3]oxazin-2-amine yielded the (4S,4aS,7aS)-4-(2-fluoro-5-nitrophenyl)-4-methyl-7a-(trifluoromethyl)-4a,5,7,7a-tetrahydro-4H-furo[3,4-e][1,3]oxazin-2-amine as a light brown foam. MS: m/z=364.0 [M+H]$^+$.

Synthesis of the Intermediate Aniline XXIVb

Intermediate XXIVb-1: Following the General Procedure F, the reduction of rel-(4S,4aS,7aS)-4-(2-fluoro-5-nitrophenyl)-4-methyl-7a-(trifluoromethyl)-4a,5,7,7a-tetrahydro-4H-furo[3,4-e][1,3]oxazin-2-amine yielded the rel-(4S,4aS,7aS)-4-(5-amino-2-fluorophenyl)-4-methyl-7a-(trifluoromethyl)-4a,5,7,7a-tetrahydro-4H-furo[3,4-e][1,3]oxazin-2-amine as an off-white solid. MS: m/z=334.2 [M+H]$^+$.

Intermediate XXIVb-2: Following the General Procedure F, the reduction of (4S,4aS,7aS)-4-(2-fluoro-5-nitrophenyl)-4-methyl-7a-(trifluoromethyl)-4a,5,7,7a-tetrahydro-4H-furo[3,4-e][1,3]oxazin-2-amine yielded the (4S,4aS,7aS)-4-(5-amino-2-fluorophenyl)-4-methyl-7a-(trifluoromethyl)-4a,5,7,7a-tetrahydro-4H-furo[3,4-e][1,3]oxazin-2-amine as a light brown foam. MS: m/z=334.2 [M+H]$^+$.

General Procedure Q for the Synthesis of the Final Examples I

To a solution of the acid XII (0.16 mmol) in MeOH (1 ml) was added at 22° C. 4-(4,6-dimethoxy-1,3,5-triazin-2-yl)-4-methyl-morpholiniumchloride (0.19 mmol) and stirring was continued at 0° C. for 30 min. To the mixture was added a solution of the aniline XI (0.15 mmol) in MeOH (2 ml) and stirring was continued at 0° C. for 4 h. The mixture was evaporated and the residue partitioned between saturated aqueous Na$_2$CO$_3$ and ethyl acetate. The organic layer was dried, evaporated and the residue was purified on preparative HPLC RP18 column using a gradient of water/NEt$_3$ (99.9:0.1)→CH$_3$CN. Alternatively, the crude material can be purified by chromatography on Si—NH$_2$ using AcOEt followed by trituration with diethyl ether to give the final examples of formula I.

Example 1

5-Chloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 5-chloro-pyridine-2-carboxylic acid following procedure G yielded the title compound as a white solid. MS: m/z=405.3 & 407.2 [M+H]$^+$.

Example 2

3,5-Dichloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 3,5-dichloro-pyridine-2-carboxylic acid following procedure G yielded the title compound as a white solid. MS: m/z=439.1 & 441.1 [M+H]$^+$.

Example 3

5-Fluoro-pyridine-2-carboxylic acid [3-((3aS,7S, 7aS)-5-amino-7-methyl-3,3a,7,7a-tetrahydro-4H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 5-fluoro-pyridine-2-carboxylic acid following procedure G yielded the title compound as a white solid. MS: m/z=389.2 [M+H]$^+$.

Example 4

5-Cyano-pyridine-2-carboxylic acid [3-((3aS,7S, 7aS)-5-amino-7-methyl-3,3a,7,7a-tetrahydro-4H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 5-cyano-pyridine-2-carboxylic acid following procedure G yielded the title compound as a white solid. MS: m/z=396.2 [M+H]$^+$.

Example 5

Pyridine-2-carboxylic acid [3-((3aS,7S,7aS)-5-amino-7-methyl-3,3a,7,7a-tetrahydro-4H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and pyridine-2-carboxylic acid following procedure G yielded the title compound as a colorless solid. MS: m/z=371.2 [M+H]$^+$.

Example 6

5-(2,2,2-Trifluoro-ethoxy)-pyridine-2-carboxylic acid [3-((3aS,7S,7aS)-5-amino-7-methyl-3,3a,7,7a-tetrahydro-4H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 5-(2,2,2-trifluoro-ethoxy)-pyridine-2-carboxylic acid (prepared as described in Banner D. et al., WO 2010/128 058) following procedure G yielded the title compound as a colorless solid. MS: m/z=469.2 [M+H]$^+$.

Example 7

5-But-2-ynyloxy-pyrazine-2-carboxylic acid [3-((3aS,7S,7aS)-5-amino-7-methyl-3,3a,7,7a-tetrahydro-4H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 5-but-2-ynyloxy-pyridine-2-carboxylic acid (prepared as described in Tamura Y. et al., WO 2010/113, 848) following procedure G yielded the title compound as a colorless solid. MS: m/z=440.4 [M+H]$^+$.

Example 8

5-(2,2,2-Trifluoro-ethoxy)-pyrazine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 5-(2,2,2-trifluoro-ethoxy)-pyrazine-2-carboxylic acid (prepared as described in Suzuki Y. et al., WO 2009/091 016) following procedure G yielded the title compound as a colorless solid. MS: m/z=470.2 [M+H]$^+$.

Example 9

5-Cyclopropylmethoxy-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 5-cyclopropylmethoxy-pyridine-2-carboxylic acid (prepared as described in Scott, J. et al., WO 2011/044181) following procedure G yielded the title compound as a colorless solid. MS: m/z=441.3 [M+H]$^+$.

Example 10

5-But-2-ynyloxy-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide 5-But-2-ynyloxy-pyridine-2-carboxylic acid methyl ester A mixture of 5-hydroxy-pyridine-2-carboxylic acid methyl ester (271 mg) and 1-bromo-2-butine (283 mg) in DMF (5 ml) was treated with potassium carbonate (367 mg) and heated to 100° C. for 16 h. the mixture was partitioned between water and ethyl acetate, the organic layer was dried, evaporated and the residue was purified by chromatography using heptane/ethyl acetate (gradient from 0-80% ethyl acetate) to give the title product (266 mg) as a pale yellow solid. MS: m/z=206.1 [M+H]$^+$.

5-But-2-ynyloxy-pyridine-2-carboxylic acid

To a solution of 5-but-2-ynyloxy-pyridine-2-carboxylic acid methyl ester (234 mg) in THF (20 ml) and water (15 ml) was added aqueous LiOH (1M, 2.3 ml) and the mixture was stirred at 22° C. for 1 h. The mixture was treated with aqueous HCl (1M, 2.3 ml), evaporated slowly, the suspension obtained was filtered, the residue washed with water and dried to give the title product (165 mg) as a white solid. MS: m/z=192.1 [M+H]$^+$.

The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 5-but-2-ynyloxy-pyridine-2-carboxylic acid following procedure G yielded the title compound as a white solid. MS: m/z=439.2 [M+H]$^+$.

Example 11

5-(2,2,3,3-Tetrafluoro-propoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 5-(2,2,3,3-tetrafluoro-propoxy)-pyridine-2-carboxylic acid (prepared as described in Banner, D. et al., WO 2011/069934) following procedure G yielded the title compound as a white solid. MS: m/z=501.1 [M+H]$^+$.

Example 12

N-(3-((4S,4aS,7aS)-2-amino-4-methyl-4a,5,7,7a-tetrahydro-4H-furo[3,4-e][1,3]oxazin-4-yl)-4-fluorophenyl)-3-chloro-5-cyanopicolinamide The coupling of (3aS,7S,7aS)-7-(5-amino-2-fluoro-phenyl)-7-methyl-3,3a,7,7a-tetrahydro-1H-2,4-dioxa-6-aza-inden-5-ylamine and 3-chloro-5-cyano-pyridine-2-carboxylic acid following procedure G yielded the title compound as a pale yellow solid. MS: m/z=430.2 [M+H]$^+$.

Example 13

5-Cyano-pyridine-2-carboxylic acid [3-((3aS,7S,7aS)-5-amino-7-fluoromethyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-fluoromethyl-3,3a,7,7a-tetrahydro-1H-2,4-dioxa-6-aza-inden-5-ylamine and 5-cyano-pyridine-2-carboxylic acid following procedure G yielded the title compound as a white solid. MS: m/z=414.1 [M+H]$^+$.

Example 14

5-Chloro-pyridine-2-carboxylic acid [3-((3aS,7S,7aS)-5-amino-7-fluoromethyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-fluoromethyl-3,3a,7,7a-tetrahydro-1H-2,4-dioxa-6-aza-inden-5-ylamine and 5-chloro-pyridine-2-carboxylic acid following procedure G yielded the title compound as a white solid. MS: m/z=423.0 [M+H]$^+$.

Example 15

5-Fluoro-pyridine-2-carboxylic acid [3-((3aS,7S,7aS)-5-amino-7-fluoromethyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-fluoromethyl-3,3a,7,7a-tetrahydro-1H-2,4-dioxa-6-aza-inden-5-ylamine and 5-fluoro-pyridine-2-carboxylic acid following procedure G yielded the title compound as a white solid. MS: m/z=407.3 [M+H]$^+$.

Example 16

5-Chloro-pyridine-2-carboxylic acid [3-((3aS,7S,7aS)-5-amino-7-difluoromethyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-difluoromethyl-3,3a,7,7a-tetrahydro-1H-2,4-dioxa-6-aza-inden-5-ylamine and 5-chloro-pyridine-2-carboxylic acid following procedure G yielded the title compound as a colorless solid. MS: m/z=441.2 [M+H]$^+$.

Example 17

5-Cyano-pyridine-2-carboxylic acid [3-((3aS,7S,7aS)-5-amino-7-difluoromethyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-difluoromethyl-3,3a,7,7a-tetrahydro-1H-2,4-dioxa-6-aza-inden-5-ylamine and 5-cyano-pyridine-2-carboxylic acid following procedure G yielded the title compound as a colorless solid. MS: m/z=432.3 [M+H]$^+$.

Example 18

5-But-2-ynyloxy-pyrazine-2-carboxylic acid [3-((3aS,7S,7aS)-5-amino-7-difluoromethyl-3,3a,7,7a-tetrahydro-1H-2,4-dioxa-6-aza-inden-7-yl)-4-fluoro-phenyl]-amide The coupling of (3aS,7S,7aS)-7-(5-amino-2-fluoro-phenyl)-7-difluoromethyl-3,3a,7,7a-tetrahydro-1H-2,4-dioxa-6-aza-inden-5-ylamine and 5-but-2-ynyloxy-pyridine-2-carboxylic acid (prepared as described in Tamura Y. et al., WO 2010/113, 848) following procedure G yielded the title compound as a colorless solid. MS: m/z=476.2 [M+H]$^+$.

Example 19

N-(3-(rel-(4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-cyanopicolinamide The coupling of rel-(4S,4aS,7aS)-4-(5-amino-2-fluorophenyl)-4-methyl-7a-(trifluoromethyl)-4a,5,7,7a-tetrahydro-4H-furo[3,4-e][1,3]oxazin-2-amine (intermediate XXIVb-1) and 5-cyano-pyridine-2-carboxylic acid following procedure G yielded the title compound as an off-white foam. MS: m/z=464.1 [M+H]$^+$.

Example 20

N-(3-(rel-(4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-(but-2-ynyloxy)pyrazine-2-carboxamide The coupling of rel-(4S,4aS,7aS)-4-(5-amino-2-fluorophenyl)-4-methyl-7a-(trifluoromethyl)-4a,5,7,7a-tetrahydro-4H-furo[3,4-e][1,3]oxazin-2-amine (intermediate XXIVb-1) and 5-(but-2-ynyloxy)pyrazine-2-carboxylic acid following procedure G yielded the title compound as a white foam. MS: m/z=508.2 [M+H]+.

Example 21

N-(3-((4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-chloropicolinamide The coupling of (4S,4aS,7aS)-4-(5-amino-2-fluorophenyl)-4-methyl-7a-(trifluoromethyl)-4a,5,7,7a-tetrahydro-4H-furo[3,4-e][1,3]oxazin-2-amine (intermediate XXIVb-2) and 5-chloro-pyridine-2-carboxylic acid following procedure G yielded the title compound as a white solid. MS: m/z=473.1 [M+H]+.

Example 22

N-(3-((4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-cyanopicolinamide The coupling of (4S,4aS,7aS)-4-(5-amino-2-fluorophenyl)-4-methyl-7a-(trifluoromethyl)-4a,5,7,7a-tetrahydro-4H-furo[3,4-e][1,3]oxazin-2-amine (intermediate XXIVb-2) and 5-cyano-pyridine-2-carboxylic acid following procedure G yielded the title compound as a white solid. MS: m/z=464.1 [M+H]+.

The invention claimed is:

1. A compound of formula I

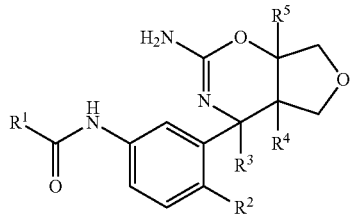

wherein
$R^1$ is selected from the group consisting of
i) aryl, and
ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
$R^2$ is selected from the group consisting of
i) hydrogen,
ii) $C_{1-6}$-alkyl, and
iii) halogen;
$R^3$ is selected from the group consisting of
i) $C_{1-6}$-alkyl, and
ii) halogen-$C_{1-6}$-alkyl;
$R^4$ is selected from the group consisting of
i) hydrogen, and
ii) $C_{1-6}$-alkyl; and
$R^5$ is selected from the group consisting of
i) hydrogen,
ii) halogen-$C_{1-6}$-alkyl, and
iii) $C_{1-6}$-alkyl;
or a pharmaceutically acceptable salt thereof.

2. The compound of claim 1, wherein
$R^1$ is selected from the group consisting of
i) aryl, and
ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
$R^2$ is selected from the group consisting of
i) hydrogen,
ii) $C_{1-6}$-alkyl, and
iii) halogen;
$R^3$ is $C_{1-6}$-alkyl;
$R^4$ is selected from the group consisting of
i) hydrogen, and
ii) $C_{1-6}$-alkyl; and
$R^5$ is selected from the group consisting of
i) hydrogen, and
ii) $C_{1-6}$-alkyl;
or a pharmaceutically acceptable salt thereof.

3. The compound of claim 1, having formula Ia,

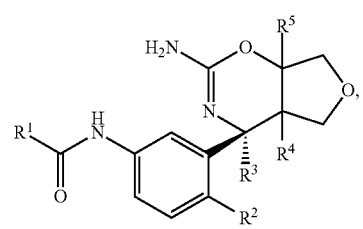

or a pharmaceutically acceptable salt thereof.

4. The compound of claim 1, having formula Ib,

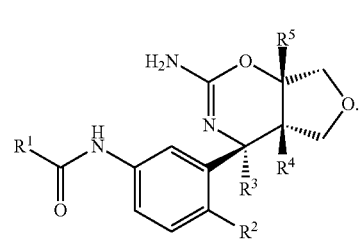

5. The compound of claim 1, wherein $R^2$ is halogen.
6. The compound of claim 5, wherein $R^2$ is F.
7. The compound of claim 1 wherein $R^3$ is $C_{1-6}$-alkyl or halogen-$C_{1-6}$-alkyl.
8. The compound of claim 7, wherein $R^3$ is $C_{1-6}$-alkyl.
9. The compound of claim 8, wherein $R^3$ is methyl.
10. The compound of claim 7, wherein $R^3$ is halogen-$C_{1-6}$-alkyl.
11. The compound of claim 10, wherein $R^3$ is —$CH_2CH_2F$ or —$CH_2CHF_2$.
12. The compound of claim 1, wherein $R^4$ is hydrogen.
13. The compound of claim 1, wherein $R^4$ is $C_{1-6}$-alkyl.
14. The compound of claim 1, wherein $R^5$ is hydrogen.
15. The compound of claim 1, wherein $R^5$ is $C_{1-6}$-alkyl.
16. The compound of claim 1, wherein $R^5$ is halogen-$C_{1-6}$-alkyl.
17. The compound of claim 16, wherein $R^5$ is —$CF_3$.

18. A pharmaceutical composition comprising a therapeutically effective amount of a compound of formula I

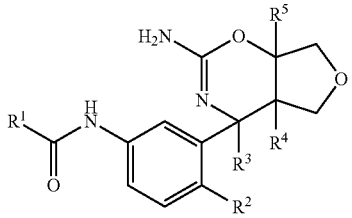

wherein
R¹ is selected from the group consisting of
i) aryl, and
ii) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
R² is selected from the group consisting of
i) hydrogen,
ii) $C_{1-6}$-alkyl, and
iii) halogen;
R³ is selected from the group consisting of
i) $C_{1-6}$-alkyl, and
ii) halogen-$C_{1-6}$-alkyl;
R⁴ is selected from the group consisting of
i) hydrogen, and
ii) $C_{1-6}$-alkyl; and
R⁵ is selected from the group consisting of
i) hydrogen,
ii) halogen-$C_{1-6}$-alkyl, and
iii) $C_{1-6}$-alkyl;
iv) or a pharmaceutically acceptable salt thereof and a pharmaceutically acceptable carrier.

19. A compound of formula I

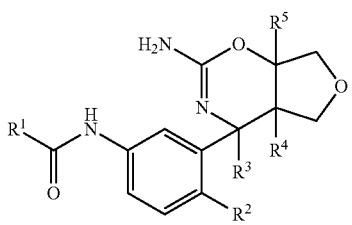

wherein
R¹ is selected from the group consisting of
v) aryl,
vi) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
vii) heteroaryl, and
viii) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;

R² is selected from the group consisting of
iv) hydrogen,
v) $C_{1-6}$-alkyl, and
vi) halogen;
R³ is
iv) halogen-$C_{1-6}$-alkyl;
R⁴ is selected from the group consisting of
iii) hydrogen, and
iv) $C_{1-6}$-alkyl; and
R⁵ is selected from the group consisting of
iv) hydrogen,
v) halogen-$C_{1-6}$-alkyl, and
vi) $C_{1-6}$-alkyl;
or a pharmaceutically acceptable salt thereof.

20. The compound of claim 19, having formula Ia,

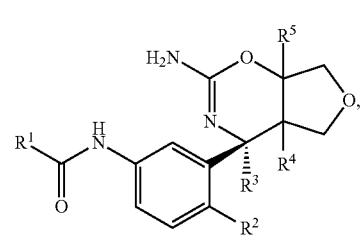

or a pharmaceutically acceptable salt thereof.

21. The compound of claim 19, having formula Ib,

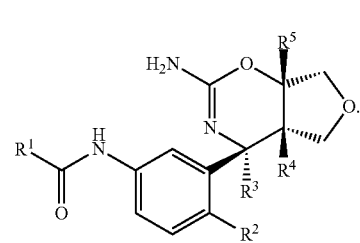

22. The compound of claim 19, wherein R² is halogen.
23. The compound of claim 22, wherein R² is F.
24. The compound of claim 19, wherein R³ is —$CH_2CH_2F$ or —$CH_2CHF_2$.
25. The compound of claim 19, wherein R⁴ is hydrogen.
26. The compound of claim 19, wherein R⁴ is $C_{1-6}$-alkyl.
27. The compound of claim 19, wherein R⁵ is hydrogen.
28. The compound of claim 19, wherein R⁵ is $C_{1-6}$-alkyl.
29. The compound of claim 19, wherein R⁵ is halogen-$C_{1-6}$-alkyl.
30. The compound of claim 29, wherein R⁵ is —$CF_3$.
31. The compound of claim 19, wherein R¹ is heteroaryl or heteroaryl substituted by 1-2 substituents individually selected from cyano, halogen, halogen-$C_{1-6}$-alkoxy and $C_{2-6}$-alkynyl-$C_{1-6}$-alkoxy.
32. The compound of claim 31, wherein R¹ is pyridinyl, pyridinyl substituted by 1-2 substituents individually selected from cyano, halogen and halogen-$C_{1-6}$-alkoxy or pyrazinyl substituted by halogen-$C_{1-6}$-alkoxy or $C_{2-6}$-alkynyl-$C_{1-6}$-alkoxy.
33. The compound of claim 32, wherein R¹ is 5-chloro-pyridine-2-yl, 3,5-dichloro-pyridine-2-yl, 5-(2,2,2-trifluoro-ethoxy)-pyrazine-2-yl, 5-(2,2,2-trifluoro-ethoxy)-pyridine-2-yl, 5-but-2-ynyloxy-pyrazine-2-yl, 5-cyano-pyridine-2-yl, 5-fluoro-pyridine-2-yl or pyridine-2-yl.

34. The compound of claim 33, wherein $R^1$ is 5-cyano-pyridine-2-yl or 5-but-2-ynyloxy-pyrazine-2-yl.

35. The compound of claim 19, selected from the group consisting of
- 5-Cyano-pyridine-2-carboxylic acid [3-((3aS,7S,7aS)-5-amino-7-fluoromethyl-3,3a,7,7a-tetrahydro-1H-2,4-dioxa-6-aza-inden-7-yl)-4-fluoro-phenyl]-amide,
- 5-Chloro-pyridine-2-carboxylic acid [3-((3aS,7S,7aS)-5-amino-7-fluoromethyl-3,3a,7,7a-tetrahydro-1H-2,4-dioxa-6-aza-inden-7-yl)-4-fluoro-phenyl]-amide,
- 5-Fluoro-pyridine-2-carboxylic acid [3-((3aS,7S,7aS)-5-amino-7-fluoromethyl-3,3a,7,7a-tetrahydro-1H-2,4-dioxa-6-aza-inden-7-yl)-4-fluoro-phenyl]-amide,
- 5-Chloro-pyridine-2-carboxylic acid [3-((3aS,7S,7aS)-5-amino-7-difluoromethyl-3,3a,7,7a-tetrahydro-1H-2,4-dioxa-6-aza-inden-7-yl)-4-fluoro-phenyl]-amide,
- 5-Cyano-pyridine-2-carboxylic acid [3-((3aS,7S,7aS)-5-amino-7-difluoromethyl-3,3a,7,7a-tetrahydro-1H-2,4-dioxa-6-aza-inden-7-yl)-4-fluoro-phenyl]-amide, and
- 5-But-2-ynyloxy-pyrazine-2-carboxylic acid [3-((3aS,7S,7aS)-5-amino-7-difluoromethyl-3,3a,7,7a-tetrahydro-1H-2,4-dioxa-6-aza-inden-7-yl)-4-fluoro-phenyl]-amide, or a pharmaceutical acceptable salt thereof.

36. A pharmaceutical composition comprising a therapeutically effective amount of a compound of formula I

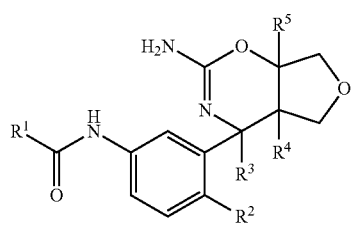

wherein
$R^1$ is selected from the group consisting of
v) aryl,
vi) aryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl,
vii) heteroaryl, and
viii) heteroaryl substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;

$R^2$ is selected from the group consisting of
iv) hydrogen,
v) $C_{1-6}$-alkyl, and
vi) halogen;

$R^3$ is halogen-$C_{1-6}$-alkyl;

$R^4$ is selected from the group consisting of
iii) hydrogen, and
iv) $C_{1-6}$-alkyl; and $R^5$ is selected from the group consisting of
v) hydrogen,
vi) halogen-$C_{1-6}$-alkyl, and
vii) $C_{1-6}$-alkyl;
viii) or a pharmaceutically acceptable salt thereof and a pharmaceutically acceptable carrier.

37. A compound of formula I

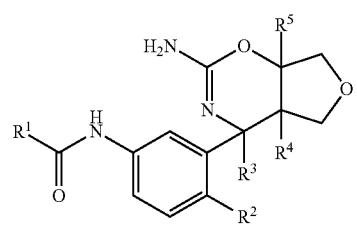

wherein
$R^1$ is selected from the group consisting of
pyrazine, and
pyrazine, substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;

$R^2$ is selected from the group consisting of
vii) hydrogen,
viii) $C_{1-6}$-alkyl, and
ix) halogen;

$R^3$ is selected from the group consisting of
v) $C_{1-6}$-alkyl, and
vi) halogen-$C_{1-6}$-alkyl;

$R^4$ is selected from the group consisting of
v) hydrogen, and
vi) $C_{1-6}$-alkyl; and $R^5$ is selected from the group consisting of
vii) hydrogen,
viii) halogen-$C_{1-6}$-alkyl, and
ix) $C_{1-6}$-alkyl;

or a pharmaceutically acceptable salt thereof.

38. The compound of claim 37, wherein
$R^1$ is selected from the group consisting of
pyrazine, and
pyrazine, substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;

$R^2$ is selected from the group consisting of
iv) hydrogen,
v) $C_{1-6}$-alkyl, and
vi) halogen;

$R^3$ is $C_{1-6}$-alkyl;

$R^4$ is selected from the group consisting of
iii) hydrogen, and
iv) $C_{1-6}$-alkyl; and $R^5$ is selected from the group consisting of
iii) hydrogen, and
iv) $C_{1-6}$-alkyl;

or a pharmaceutically acceptable salt thereof.

39. The compound of claim 37, having formula Ia,

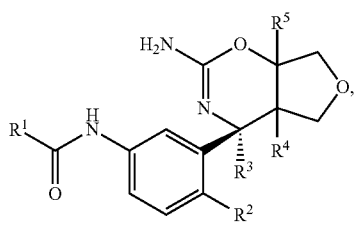

or a pharmaceutically acceptable salt thereof.

40. The compound of claim 37, having formula Ib,

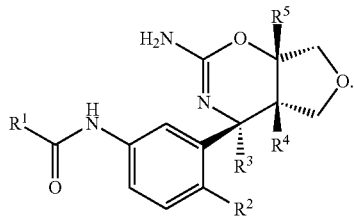

41. The compound of claim 37, wherein $R^2$ is halogen.
42. The compound of claim 37, wherein $R^2$ is F.
43. The compound of claim 37 wherein $R^3$ is $C_{1-6}$-alkyl or halogen-$C_{1-6}$-alkyl.
44. The compound of claim 43, wherein $R^3$ is $C_{1-6}$-alkyl.
45. The compound of claim 44, wherein $R^3$ is methyl.
46. The compound of claim 43, wherein $R^3$ is halogen-$C_{1-6}$-alkyl.
47. The compound of claim 46, wherein $R^3$ is —$CH_2CH_2F$ or —$CH_2CHF_2$.
48. The compound of claim 37, wherein $R^4$ is hydrogen.
49. The compound of claim 37, wherein $R^4$ is $C_{1-6}$-alkyl.
50. The compound of claim 37, wherein $R^5$ is hydrogen.
51. The compound of claim 37, wherein $R^5$ is $C_{1-6}$-alkyl.
52. The compound of claim 37, wherein $R^5$ is halogen-$C_{1-6}$-alkyl.
53. The compound of claim 52, wherein $R^5$ is —$CF_3$.
54. The compound of claim 37, wherein $R^1$ is pyrazinyl substituted by halogen-$C_{1-6}$-alkoxy or $C_{2-6}$-alkynyl-$C_{1-6}$-alkoxy.
55. The compound of claim 54, wherein $R^1$ is 5-but-2-ynyloxy-pyrazine-2-yl.
56. The compound of claim 37, selected from the group consisting of
5-But-2-ynyloxy-pyrazine-2-carboxylic acid [3-((3aS,7S, 7aS)-5-amino-7-methyl-3,3a,7,7a-tetrahydro-1H-2,4-dioxa-6-aza-inden-7-yl)-4-fluoro-phenyl]-amide,
5-But-2-ynyloxy-pyrazine-2-carboxylic acid [3-((3aS,7S, 7aS)-5-amino-7-difluoromethyl-3,3a,7,7a-tetrahydro-1H-2,4-dioxa-6-aza-inden-7-yl)-4-fluoro-phenyl]-amide,
N-(3-(rel-(4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-(but-2-ynyloxy)pyrazine-2-carboxamide,
5-(2,2,2-Trifluoro-ethoxy)-pyrazine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-(2,2,2-Trifluoro-ethoxy)-pyrazine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, and
5-But-2-ynyloxy-pyrazine-2-carboxylic acid [3-((3aS,7S, 7aS)-5-amino-7-methyl-3,3a,7,7a-tetrahydro-1H-2,4-dioxa-6-aza-inden-7-yl)-4-fluoro-phenyl]-amide,
or a pharmaceutical acceptable salt thereof.

57. A pharmaceutical composition comprising a therapeutically effective amount of a compound of formula I

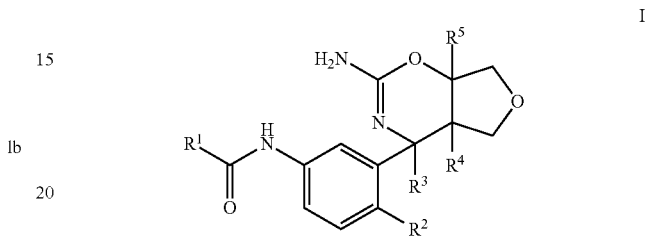

wherein
$R^1$ is selected from the group consisting of
  pyrazine, and
  pyrazine substituted by 1-4 substituents individually selected from cyano, cyano-$C_{1-6}$-alkyl, halogen, halogen-$C_{1-6}$-alkoxy, halogen-$C_{1-6}$-alkyl, $C_{1-6}$-alkoxy, $C_{1-6}$-alkoxy-$C_{1-6}$-alkyl, $C_{2-6}$-alkynyl-$C_{1-6}$-alkoxy, $C_{2-6}$-alkynyl and $C_{1-6}$-alkyl;
$R^2$ is selected from the group consisting of
vii) hydrogen,
viii) $C_{1-6}$-alkyl, and
ix) halogen;
$R^3$ is selected from the group consisting of
iii) $C_{1-6}$-alkyl, and
iv) halogen-$C_{1-6}$-alkyl;
$R^4$ is selected from the group consisting of
v) hydrogen, and
vi) $C_{1-6}$-alkyl; and
$R^5$ is selected from the group consisting of
ix) hydrogen,
x) halogen-$C_{1-6}$-alkyl, and
xi) $C_{1-6}$-alkyl;
xii) or a pharmaceutically acceptable salt thereof and a pharmaceutically acceptable carrier.

58. A compound selected from the group consisting of
5-Fluoro-pyridine-2-carboxylic acid [3-((3aS,7S,7aS)-5-amino-7-methyl-3,3a,7,7a-tetrahydro-1 H-2,4-dioxa-6-aza-inden-7-yl)-4-fluoro-phenyl]-amide,
5-Cyclopropylmethoxy-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl] amide,
5-But-2-ynyloxy-pyridine-2-carboxylic acid [3-((3aS,7S, 7aS)-5-amino-7-methyl-3,3a,7,7a-tetrahydro-1H-2,4-dioxa-6-aza-inden-7-yl)-4-fluoro-phenyl]amide,
N-(3-(rel-(4SR,4aSR,7aSR)-2-amino-4-methyl-7a-(trifluoromethyl)-4a,5,7,7a-tetrahydro-4H-furo[3,4-e][1,3] oxazin-4-yl)-4-fluorophenyl)-5-cyanopicolinamide,
N-(3-((4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-chloropicolinamide,
N-(3-((4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-cyanopicolinamide, 5-(2,2,2-Trifluoro-ethoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-(2,2,3,3-Tetrafluoro-propoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, N-(3-((4S,4aS,7aS)-2-amino-4-methyl-4a,5,7,7a-tetrahydro-4H-furo[3,4-e][1,3]oxazin-4-yl)-4-fluorophenyl)-3-chloro-5-cyanopicolinamide, Pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 3,5-Dichloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-Chloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 3,5-Dichloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-(2,2,2-Trifluoro-ethoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-Fluoro-pyridine-2-carboxylic acid [3-((3aS,7S,7aS)-5-amino-7-methyl-3,3a,7,7a-tetrahydro-1 H-2,4-dioxa-6-aza-inden-7-yl)-4-fluoro-phenyl]-amide, and Pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, or a pharmaceutical acceptable salt thereof.

59. A pharmaceutical composition comprising a therapeutically effective amount of a compound selected from the group consisting of 5-Fluoro-pyridine-2-carboxylic acid [3-((3aS,7S,7aS)-5-amino-7-methyl-3,3a,7,7a-tetrahydro-1 H-2,4-dioxa-6-aza-inden-7-yl)-4-fluoro-phenyl]-amide, 5-Cyclopropylmethoxy-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-But-2-ynyloxy-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, N-(3-(rel-(4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-cyanopicolinamide, N-(3-((4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-chloropicolinamide, N-(3-((4SR,4aSR,7aSR)-2-amino-4-methyl-7a-(trifluoromethyl)-4a,5,7,7a-tetrahydro-4H-furo[3,4-e][1,3]oxazin-4-yl)-4-fluorophenyl)-5-cyanopicolinamide, 5-(2,2,2-Trifluoro-ethoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-(2,2,3,3-Tetrafluoro-propoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, N-(3-((4S,4aS,7aS)-2-amino-4-methyl-4a,5,7,7a-tetrahydro-4H-furo[3,4-e][1,3]oxazin-4-yl)-4-fluorophenyl)-3-chloro-5-cyanopicolinamide, Pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 3,5-Dichloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-Chloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 3,5-Dichloro-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-(2,2,2-Trifluoro-ethoxy)-pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, 5-Fluoro-pyridine-2-carboxylic acid [3-((3aS,7S,7aS)-5-amino-7-methyl-3,3a,7,7a-tetrahydro-1 H-2,4-dioxa-6-aza-inden-7-yl)-4-fluoro-phenyl]-amide, and Pyridine-2-carboxylic acid [3-((3aS,7S,7aS)-5-amino-7-methyl-3,3a,7,7a-tetrahydro-1H-2,4-dioxa-6-aza-inden-7-yl)-4-fluoro-phenyl]-amide, or a pharmaceutical acceptable salt thereof and a pharmaceutically acceptable carrier.

\* \* \* \* \*